United States Patent
Piorek et al.

(10) Patent No.: US 7,916,834 B2
(45) Date of Patent: Mar. 29, 2011

(54) SMALL SPOT X-RAY FLUORESCENCE (XRF) ANALYZER

(75) Inventors: Stanislaw Piorek, Hillsborough, NJ (US); Mark Hamilton, Upton, MA (US); Kenneth P. Martin, Watertown, MA (US); Pratheev Sreetharan, Medford, MA (US); Michael E. Dugas, Londonderry, NH (US); Paul Estabrooks, Monson, MA (US); Lee Grodzins, Lexington, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 0 days.

(21) Appl. No.: 12/029,410

(22) Filed: Feb. 11, 2008

(65) Prior Publication Data

US 2008/0192897 A1  Aug. 14, 2008

Related U.S. Application Data

(60) Provisional application No. 60/889,465, filed on Feb. 12, 2007.

(51) Int. Cl.
*G01N 23/223* (2006.01)

(52) U.S. Cl. ........... 378/44; 378/45; 378/48; 378/50; 378/102; 378/148; 378/160; 378/197; 378/207

(58) Field of Classification Search ............ 378/44, 378/45, 48, 50, 102, 148, 160, 197, 207
See application file for complete search history.

(56) References Cited

U.S. PATENT DOCUMENTS

| | | | | |
|---|---|---|---|---|
| 4,962,517 | A | * | 10/1990 | Koga .................... 378/48 |
| 5,033,074 | A | * | 7/1991 | Cotter et al. ............ 378/147 |
| 5,220,169 | A | * | 6/1993 | Ninomiya et al. ........ 250/358.1 |

(Continued)

FOREIGN PATENT DOCUMENTS

EP  0396291 B1  11/1994

(Continued)

OTHER PUBLICATIONS

Kaufmann, et al., "Measurement & Monitoring: 15th Quarterly Literature Update.," SAGEEP 2004: Symposium on the Application of Geophysics to Engineering and Environmental Problems, p. 1-145, (2004).

(Continued)

*Primary Examiner* — Hoon Song
*Assistant Examiner* — Mona M Sanei
(74) *Attorney, Agent, or Firm* — Charles B. Katz

(57) ABSTRACT

A hand-held, self-contained x-ray fluorescence (XRF) analyzer produces a small x-ray spot on a sample to interrogate the elemental composition of a sample region of millimeter-size characteristic dimension. The analyzer includes a collimator for aiming an x-ray beam toward a desired location on the sample and for determining the size of the spot produced on the sample. The analyzer may include a digital camera oriented toward the portion of the sample that is, or would be, interrogated by the x-ray spot to facilitate aiming the analyzer. The analyzer may generate a reticule in a displayed image to indicate the portion of the sample that is, or would be, illuminated by the x-ray beam. The analyzer may automatically annotate the image of the sample with text or graphics that contain information about the analyzed sample. The image may be stored in the hand-held analyzer or provided for external storage or display.

11 Claims, 22 Drawing Sheets

U.S. PATENT DOCUMENTS

| | | | | |
|---|---|---|---|---|
| 5,462,078 | A | * | 10/1995 | Andenmatten et al. ....... 137/209 |
| 5,910,975 | A | | 6/1999 | Floyd et al. |
| 6,141,400 | A | * | 10/2000 | Schardt et al. ................ 378/124 |
| 6,459,767 | B1 | * | 10/2002 | Boyer ........................... 378/121 |
| 6,855,930 | B2 | * | 2/2005 | Okuda et al. .................. 250/310 |
| 6,909,770 | B2 | * | 6/2005 | Schramm et al. ............... 378/45 |
| 7,236,568 | B2 | | 6/2007 | Dinsmore et al. |
| 2002/0138017 | A1 | * | 9/2002 | Bui et al. ....................... 600/537 |
| 2003/0215060 | A1 | * | 11/2003 | Ohzawa ........................ 378/154 |
| 2004/0041998 | A1 | * | 3/2004 | Haddad ............................ 356/71 |
| 2004/0247076 | A1 | * | 12/2004 | Navab et al. .................... 378/63 |
| 2005/0053199 | A1 | * | 3/2005 | Miles ............................ 378/197 |
| 2005/0113682 | A1 | * | 5/2005 | Webber et al. ................ 600/426 |
| 2005/0226373 | A1 | * | 10/2005 | Trombka et al. ................ 378/44 |
| 2005/0286683 | A1 | * | 12/2005 | Cantu ......................... 378/98.12 |
| 2006/0139372 | A1 | * | 6/2006 | Orofino ......................... 345/629 |
| 2007/0081627 | A1 | * | 4/2007 | Bates ............................... 378/62 |
| 2007/0269003 | A1 | * | 11/2007 | Puusaari et al. ................ 378/44 |
| 2008/0152079 | A1 | * | 6/2008 | Tannian et al. ................. 378/45 |

FOREIGN PATENT DOCUMENTS

WO  WO 2006/060347  6/2006

OTHER PUBLICATIONS

Thermo Electron Corp., "NITON XLt 898He," Product Specification, Thermo Electron Corp., 2 pgs. (2006).

NITON LLC., "NITON XLp 300 Series Lead Analyzer," Product Announcement, NITON LLC, 2 pgs., (2004).

Bucksbaum, et al., "The phonon Bragg switch: a proposal to generate sub-picosecond X-ray pulses," Solid State Communications, vol. 111, p. 535-539, (1999).

Chaleard, et al., "Correction of Matrix Effects in Quantitative Elemental Analysis with Laser Ablation Optical Emission Spectrometry," J. Analytical Atomic Spectrometry, vol. 12, p. 183-188, (1997).

NITON LLC., "XLi 800 Series: The New Standard in Portable Alloy Analysis Instrumentation," Product Introduction, NITON LLC., 2 pgs., (2002).

Thermo Electron Corp., "The NITON XLt 797X: Portable Handheld Small Spot Analyzer for RoHS Compliance," GlobalTronics 2006, Technology Forum, p. 41 pgs., (2006).

Piorek, Stanislaw, "Feasibility of Analysis and Screening of Plastics for Heavy Metals with Portable X-Ray Fluorescence Analyzer with Miniature X-Ray Tube," Global Plastics Environmental Conference, 9 pgs., (2004).

Grogoriev, et al., "Subnanosecond piezoelectric x-ray switch," Applied Physics Letters, vol. 89 (No. 021109), 3 pgs., (2006).

Theromo Electron Corp., "The XRF Analysis Process in Brief," Product Brochure, Thermo Electron Corp., 2 pgs., (2006).

Innov-X Systems SmartBeam Alloy Analyzer Application Sheet, Innov-X Systems Inc., Woburn, MA 01801, Nov. 2003.

* cited by examiner (Section B-B)

(Section A-A)

```
┌─────────────────────────────┐
│ Measure the composition of  │
│ a plurality of distinct locations │
│  on a calibration target    │
│           2900              │
└─────────────────────────────┘
              │
              ▼
┌─────────────────────────────┐
│ Fit a curve to the measurements │
│           2902              │
└─────────────────────────────┘
              │
              ▼
┌─────────────────────────────┐
│  Make a reticule respond to a │
│      peak in the curve      │
│           2904              │
└─────────────────────────────┘
```

*FIG. 26*

SMALL SPOT X-RAY FLUORESCENCE (XRF) ANALYZER

RELATED APPLICATIONS

This application claims the benefit of U.S. Provisional Patent Application No. 60/889,465, filed Feb. 12, 2007, titled "Small Spot X-Ray Fluorescence (XRF) Analyzer" by Piorek, et al., the contents of which are hereby incorporated by reference.

TECHNICAL FIELD

The present invention relates to hand-held x-ray fluorescence analyzers and, more particularly, to such analyzers that illuminate a small spot on a sample with x-rays.

BACKGROUND ART

Analyzing chemical composition of samples is important in many contexts, including identifying and segregating metal types in metal recycling facilities, quality control testing in factories and forensic work. Several analytical methods are available. One common analysis method employs x-ray fluorescence (XRF). When exposed to high energy primary x-rays from a source, each atomic element present in a sample produces a unique set of characteristic fluorescence x-rays that are essentially a fingerprint for the specific element. An x-ray fluorescence analyzer determines the chemistry of a sample by illuminating a spot on the sample with x-rays and measuring the spectrum of characteristic x-rays emitted by the different elements in the sample. The primary source of x-rays may be an x-ray tube or a radioactive material, such as a radioisotope.

The term x-rays, as used herein, includes photons of energy between about 1 keV and about 150 keV and will, therefore, include: the characteristic x-rays emitted by an excited atom when it deexcites; bremsstrahlung x-rays emitted when an electron is scattered by an atom; elastic and inelastically scattered photons generally referred to as Rayleigh and Compton scattered radiation, respectively; and gamma rays in this energy range emitted when an excited nucleus deexcites.

When exposed to high energy primary x-rays from a source, each atomic element present in a sample produces a unique set of characteristic fluorescence x-rays that are essentially a fingerprint for the specific element. An x-ray fluorescence analyzer determines the chemistry of a sample by illuminating a spot on the sample with x-rays and measuring the spectrum of characteristic x-rays emitted by the various elements in the sample. The primary source of x-rays may be an x-ray tube or a radioactive material, such as a radioisotope.

At the atomic level, a characteristic fluorescent x-ray is created when a photon of sufficient energy strikes an atom in the sample, dislodging an electron from one of the atom's inner orbital shells. The atom then nearly instantaneously regains stability, filling the vacancy left in the inner orbital shell with an electron from one of the atom's higher energy (outer) orbital shells. Excess energy may be released in the form of a fluorescent x-ray, of an energy characterizing the difference between two quantum states of the atom.

By inducing and measuring a wide range of different characteristic fluorescent x-rays emitted by the different elements in the sample, XRF analyzers are able to determine the elements present in the sample, as well as to calculate their relative concentrations based on the number of fluorescent x-rays occurring at specific energies. When samples with known ranges of chemical composition, such as common grades of metal alloys, are tested, an XRF analyzer can also identify the sample by name, by referencing a programmed table or library of known materials.

It is important to note that, except in special circumstances, low concentrations of light elements (low proton or Z number elements) cannot typically be measured directly with portable XRF analyzers, because fluorescent x-rays with energies below about 2.5 kiloelectron volts (keV) are absorbed within short path lengths of air. For this reason, light element XRF analysis requires either a helium gas purge or the evacuation of the volumes through which the relevant x-rays pass.

The size of the x-ray spot on the sample determines how much of a sample is analyzed. In some cases, a small x-ray spot would be desirable. For example, a user who analyzes small components and solder joints on printed circuit boards (such as in recycling facilities) would benefit from using a hand-held XRF analyzer that produces a very small spot, so a component or solder joint of interest could be analyzed without the fluorescing x-rays illuminating surrounding components and, therefore, confusing the chemical composition of the item under test with the chemical compositions of surrounding materials. In another example, analyzing a series of small, spaced-apart portions of a sample would enable a user to gauge the homogeneity of the sample.

SUMMARY OF THE INVENTION

An embodiment of the present invention provides a hand-held, self-contained, test instrument for analyzing composition of a sample. The test instrument includes a source for producing a beam of penetrating radiation for illuminating a spot on at least a portion of the sample, thereby producing a response signal from the sample. The source may include an x-ray source, such as an x-ray tube. In other cases, the source may include a radioisotope or another gamma ray source. The analyzer includes a collimator for the beam. The collimator has a distal exit aperture characterized by a transverse dimension. The transverse dimension may be less than about 8 mm, about 3 mm, about 1 mm or about 0.3 mm. The distal exit is disposed at a distance from the sample no greater than about twice the transverse dimension. In some cases, the distal exit is disposed at a distance from the sample no greater than about the transverse dimension. The distal exit aperture may be substantially parallel to a surface of the sample that is to be analyzed. The test instrument includes a detector for receiving the response signal and for producing an output signal. The test instrument also includes a processor coupled to the detector and programmed to process the output signal from the detector, and a battery powering the source and the processor.

The collimator may include a tubular collimator. A distal end portion of the collimator nearest the sample may have a wall thickness less than the remainder of the collimator. The distal end portion of the collimator may be tapered and/or stepped. The collimator may have a circular or non-circular internal cross-sectional shape.

The test instrument may also include a shutter located between the source and the sample. The shutter may selectively allow the beam to illuminate the spot or prevent the beam from illuminating the spot. The collimator and the shutter may move together between at least two positions. In the first position, the beam passes through the collimator to illuminate the spot. In the second position, the beam is prevented from illuminating the spot. In the second position, the shutter may fluoresce the beam, and the fluoresced radiation may be directed along a path toward the detector without striking the sample.

The test instrument may also include a second collimator for the beam. The second beam collimator has a second distal exit aperture characterized by a second transverse dimension. When the beam passes through the second collimator to illuminate the spot, the second distal exit is disposed at a distance from the sample no greater than about twice the second transverse dimension. The second transverse dimension may be less than about 8 mm, about 3 mm, about 1 mm or about 0.3 mm. The collimator and the second collimator may move together between at least two positions. In the first position, the beam passes through the collimator to illuminate the spot. The distal exit apertures of the two collimators may be substantially parallel to a surface of the sample that is to be analyzed. In the second position, the beam passes through the second collimator to illuminate the spot. The test instrument may also include a shutter between the source and the sample. The shutter may selectively allow the beam to illuminate the spot or prevent the beam from illuminating the spot. The collimator, the second collimator and the shutter may move together among at least three positions. In at least one of the positions, the shutter prevents the beam from illuminating the spot.

The test instrument may also include a shutter that defines an hole. The collimator and the shutter may move together among at least three positions. In the first position, the beam passes through the collimator to illuminate the spot. In the second position, the beam passes through the hole to illuminate the spot. In the third position, the shutter prevents the beam from illuminating the spot.

Another embodiment of the present invention provides a hand-held, self-contained, test instrument for analyzing the composition of a sample. The test instrument includes a source for producing a beam of penetrating radiation for illuminating a spot on at least a portion of the sample, thereby producing a response signal from the sample. The test instrument also includes a source collimator for the beam. The source collimator has a distal exit aperture characterized by a transverse dimension. The distal exit is disposed at a distance from the sample no greater than about twice the transverse dimension. The test instrument also includes a detector for receiving the response signal and for producing an output signal. The test instrument also includes a detector collimator positioned along a light path between the spot and the detector. The response signal passes through the detector collimator before reaching the detector. The test instrument also includes a processor coupled to the detector and programmed to process the output signal from the detector. A battery in the test instrument powers the source and the processor.

Yet another embodiment of the present invention provides a hand-held, self-contained, test instrument for analyzing composition of a sample. The test instrument includes a source for producing a beam of penetrating radiation for illuminating a spot on at least a portion of the sample, thereby producing a response signal from the sample, and a detector for receiving the response signal and for producing an output signal. The test instrument also includes a processor coupled to the detector. The processor is programmed to process the output signal from the detector. A digital camera within the test instrument is oriented toward the portion of the sample. A battery in the test instrument powers the source, the processor and the camera.

The test instrument may include a display screen on which an image captured by the camera may be displayed. The display screen may be a portion of a PDA attached to the test instrument. The battery may power the display screen. The test instrument may include a data port for providing data representing an image captured by the camera to an external device. The processor may be programmed to perform a flattening algorithm on an image captured by the camera. The processor may be programmed to insert a reticule into an image captured by the camera. The reticule may indicate a location of the spot. The test instrument may include a laser that is oriented to project a visible spot on the sample in a location that corresponds with the spot of penetrating radiation. The test instrument may include a fluorescent screen between the source and the sample. The screen may include a material that produces visible light when illuminated by the beam. The processor may be programmed to include results from processing the output signal from the detector in an image captured by the camera.

An embodiment of the present invention provides a hand-held, self-contained, test instrument for analyzing composition of a sample. The test instrument includes a source for producing a beam of penetrating radiation for illuminating a spot on at least a portion of the sample, thereby producing a response signal from the sample and a detector for receiving the response signal and for producing an output signal. The test instrument includes a chamber through which the beam and the response signal pass. The test instrument further includes a coupling for receiving an end of a purge gas tank and a fluid communication path between the tank coupling and the chamber. The test instrument includes a processor coupled to the detector. The processor is programmed to process the output signal from the detector. A battery in the test instrument powers the source and the processor. A detachable portion of the test instrument may house the battery and the tank.

Another embodiment of the present invention provides a hand-held, self-contained, test instrument for analyzing composition of a sample. The test instrument includes a source for producing a beam of penetrating radiation for illuminating a spot on at least a portion of the sample, thereby producing a response signal from the sample, and a detector for receiving the response signal and for producing an output signal. The test instrument includes a processor coupled to the detector. The processor is programmed to process the output signal from the detector. A battery in the test instrument powers the source and the processor. The test instrument includes a chamber through which the beam and the response signal pass and a sensor operative to detect an amount of ambient gas present in the chamber.

The sensor may be operative to detect argon in the chamber, a flow rate of a purge gas entering the chamber and/or a gas pressure in the chamber.

Another embodiment of the present invention provides a calibration target that includes a sheet having at least three adjacent portions. The portions have a common vertex, and each portion has a vertex angle. The sum of the vertex angles is about 360 degrees. Each portion includes a material that is distinguishable from the materials of the other portions by x-ray fluorescence analysis. Each portion may be pie shaped. Each of the portions may be made of copper, nickel, iron, zinc or aluminum.

Yet another embodiment of the present invention provides a calibration target that includes a copper plug having a diameter of about 3.5 mm attached to a sheet comprising a material that is distinguishable from copper via x-ray fluorescence analysis. The sheet may include a solid polymer; the solid polymer may include a small amount of a distinct material, such as about 5% titanium.

An embodiment of the present invention provides a method for calibrating a location on a reticule in an x-ray fluorescence analyzer. The method includes aiming the analyzer at a portion of a calibration target and measuring composition of the portion of the calibration target. If the measured composition is not within a desired range, the analyzer is repositioned, with respect to the calibration target, and the measurement is repeated at the repositioned location. On the other hand, if the measured composition is within the desired range, the location of the reticule is made to correspond to a predetermined location on the calibration target.

Another embodiment of the present invention provides a method for calibrating a location on a reticule in an x-ray fluorescence analyzer. The method includes measuring composition of portions of a calibration target at a plurality of distinct locations on the calibration target, yielding a plurality of measurements and fitting a curve to the plurality of measurements. The location of the reticule is made to correspond to a predetermined location on the curve. The curve may be a paraboloid, and the composition may be measured at least five distinct locations on the calibration target.

Yet another embodiment of the present invention provides a method for analyzing composition of a sample. The method includes exposing at least a portion of the sample to a beam of penetrating radiation that produces a response signal from the sample and detecting the response signal. The method also includes producing an output signal from the response signal and processing the output signal to determine the composition of the sample. The method further includes obtaining a digital image of the at least a portion of the sample and storing a record of the digital image along with a representation of the determined composition of the sample. The sample may be analyzed by a hand-held, self-contained analyzer.

BRIEF DESCRIPTION OF THE DRAWINGS

The invention will be more fully understood by referring to the following Detailed Description of Specific Embodiments in conjunction with the Drawings, of which:

FIG. 26 is a flowchart describing use of a calibration target to calibrate a reticule, according to another embodiment of the present invention.

DETAILED DESCRIPTION OF SPECIFIC EMBODIMENTS

Figure 1:
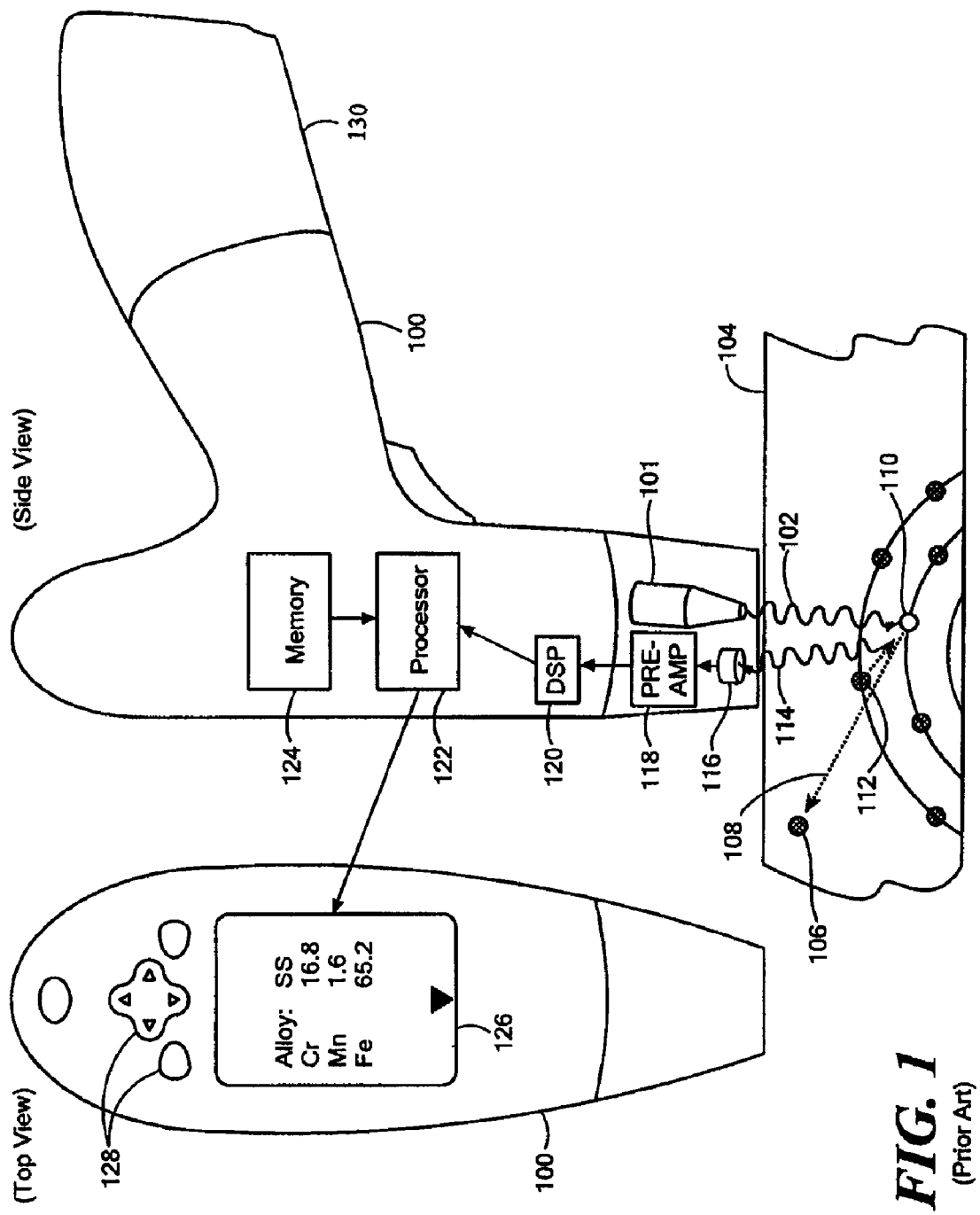
FIG. 1 is a schematic diagram of a prior-art, self-contained, hand-held XRF analyzer in use.

In accordance with embodiments of the present invention, methods and apparatus are disclosed for producing a small spot of penetrating radiation on a sample to facilitate XRF analysis of the sample or a portion thereof with a hand-held analyzer. The analyzer includes a collimator for aiming a beam of penetrating radiation toward a desired location on the sample and for determining the size of the spot produced on the sample. The collimator includes a shutter for selectively allowing the beam to illuminate the sample or blocking the beam and, thereby, preventing illumination of the sample by the beam. The size of the spot may be fixed or adjustable.

Although various types of beams may be used to strike a surface of a sample and, thereby, produce a fluorescent x-ray, for simplicity of explanation, embodiments using x-ray beams are described. However, any suitable beam of penetrating radiation may be used to illuminate a spot on the surface to produce a response signal from the sample and, thereby, interrogate the elemental composition of a region of the sample. Such a beam may be a gamma-ray beam, such as one generated by a radioactive isotope.

A hand-held XRF analyzer may include a second collimator between a sample and a detector to limit spurious fluorescent and reflected primary x-rays observed by the detector.

The hand-held XRF analyzer may include a digital camera oriented toward the portion of the sample that is, or would be, illuminated within the perimeter of the x-ray spot. The camera, together with a display of an image produced by the camera, facilitates aiming the analyzer, such that the x-ray beam illuminates a desired portion of the sample. A flattening process may be applied to the image to correct image distortion introduced by the camera's location and aim, relative to the x-ray spot. Optionally, the analyzer includes a reticle in the displayed image to indicate the portion of the sample that is, or would be, illuminated by the x-ray beam, i.e., to indicate the size and location of the x-ray spot.

Methods and apparatus are disclosed for calibrating the reticle, so the reticle accurately reflects the position, size and/or shape of the x-ray spot.

In the image, the analyzer may include text or graphics that contain information about the analyzed sample. This information may include the chemical composition of the tested portion of the sample, the date and time of the testing, the user's name, notes entered by the user (such as the source of the sample) and the like. The image may be stored in the hand-held analyzer or provided for external storage or display. Consequently, the hand-held analyzer may produce an archive record containing both an image of the portion of the sample that is analyzed and an analysis of the tested portion of the sample. The image may be a still image or a video clip of the sample being analyzed. Optionally, the image may be stored separate from, but associated with, the analysis information. For example, the image or the analysis information may include a pointer (such as a uniform resource locator (URL)) or other reference to the other.

To enable the analyzer to measure light atomic weight elements, helium gas may be used to purge air from a chamber within the analyzer. Various mechanisms may monitor the flow rate or presence of a purge gas or presence of ambient gas (air or a constituent thereof) in the chamber and automatically adjust the flow rate of the purge gas or warn a user of the presence of ambient gas in the chamber. Alternatively, the chamber may be evacuated of a substantial amount of air otherwise present in the chamber.

Chemical Analysis using X-Ray Fluorescence (XRF)

FIG. 1 is a schematic diagram of a prior-art self-contained, hand-held XRF analyzer 100 in use. FIG. 1 shows both a top view and a side view of the hand-held analyzer 100. A primary x-ray source 101 produces an x-ray beam 102 directed at the surface of the sample 104. The energy of the primary x-ray beam 102 causes inner-shell electrons (shown enlarged in FIG. 1) to be ejected from their orbits in individual atoms of the sample 104. For example, an electron 106 is ejected from an inner (lower energy) shell, as indicated by an arrow 108. A vacancy 110 left by the ejected electron 106 is filled by an electron 112 from an outer (higher energy) shell. The energy difference between the two energy shells involved in the process is generally emitted in the form of x-ray radiation, i.e., a fluorescent x-ray 114. The energy difference is characteristic of the element from which the electron 106 is emitted. Measuring the energy and intensity of the fluorescent x-ray 114 enables the element to be identified and quantified, respectively.

A detector 116 registers individual x-ray events and sends electrical signals to a preamplifier 118. The preamplifier 118 amplifies the signals from the detector 116 and sends the amplified signals to a digital signal processor (DSP) 120. The DSP 120 collects and digitizes the x-ray events occurring over time and sends resulting spectral data to a main processor 122. The processor 122 mathematically analyzes the spectral data and produces a detailed composition analysis. The resulting composition analysis may be compared against an internal table stored in a memory 124 to determine an alloy grade or other designation for the tested sample 104. Results of the analysis are displayed on a touchscreen 126 on the top portion of the hand-held analyzer 100 and, optionally, stored in the memory 124. Buttons and other controls, such as those indicated at 128, and the touchscreen 126, enable a user to interact with the processor 122. A detachable rechargeable battery 130 powers the processor 122 and other electrical components within the analyzer 100.

Figure 9:
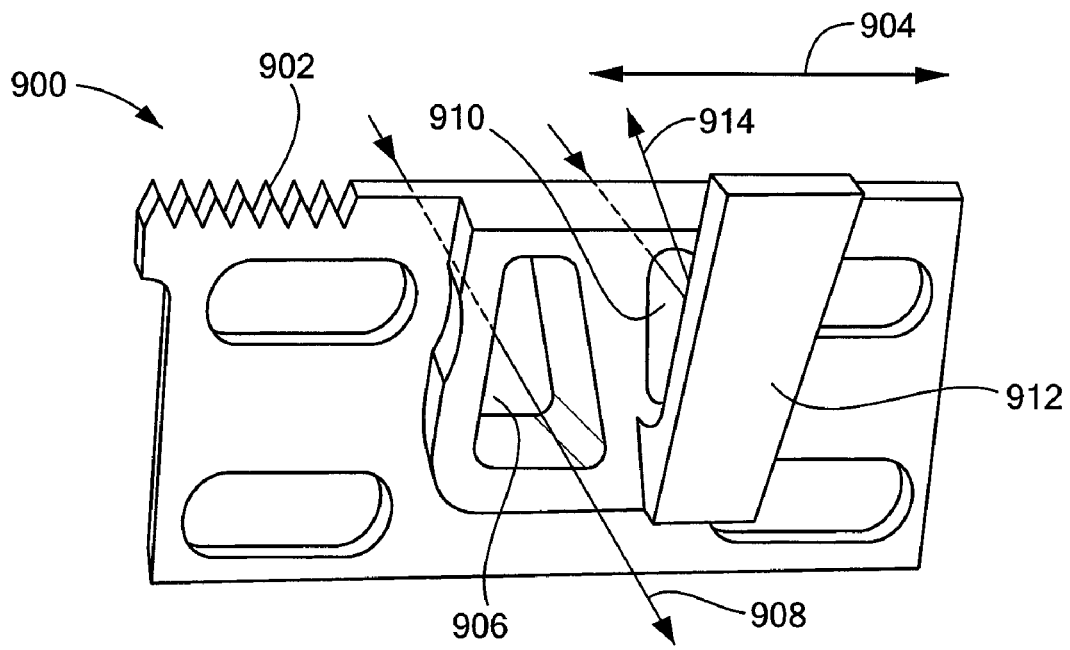
FIG. 9 is a perspective view of a prior-art shutter.

The prior-art analyzer 100 includes a shutter to selectively enable or prohibit the primary x-ray beam 102 from exiting the analyzer and striking the surface of the sample 104. FIG. 9 is a perspective view of such a prior-art shutter 900. The shutter includes a gear rack 902, which may be engaged by a spur gear (not shown) to translate the shutter 900 laterally (as indicated by an arrow 904) between two positions. In one position, the x-ray beam 102 passes through a first hole 906, as indicated by an arrow 908, and strikes the surface of the sample 104. In the other shutter position, the x-ray beam passes through a second hole 910 and interacts with a calibration sample on the back side of an angled portion 912, which produces a calibration spectrum directed toward a detector, as indicated by an arrow 914. Thus, when the shutter 900 is in the second position, the x-ray beam does not exit the analyzer 100. Instead, the x-ray beam is used to produce a calibration spectrum to calibrate the analyzer 100.

The prior-art analyzer 100 is incapable of producing a small x-ray spot on the sample. As noted, illuminating a sample with a small x-ray spot would facilitate analyzing a small sample or a small portion of a sample, such as a component or a solder joint on a printed circuit board.

Small X-Ray Spot

Figure 2:
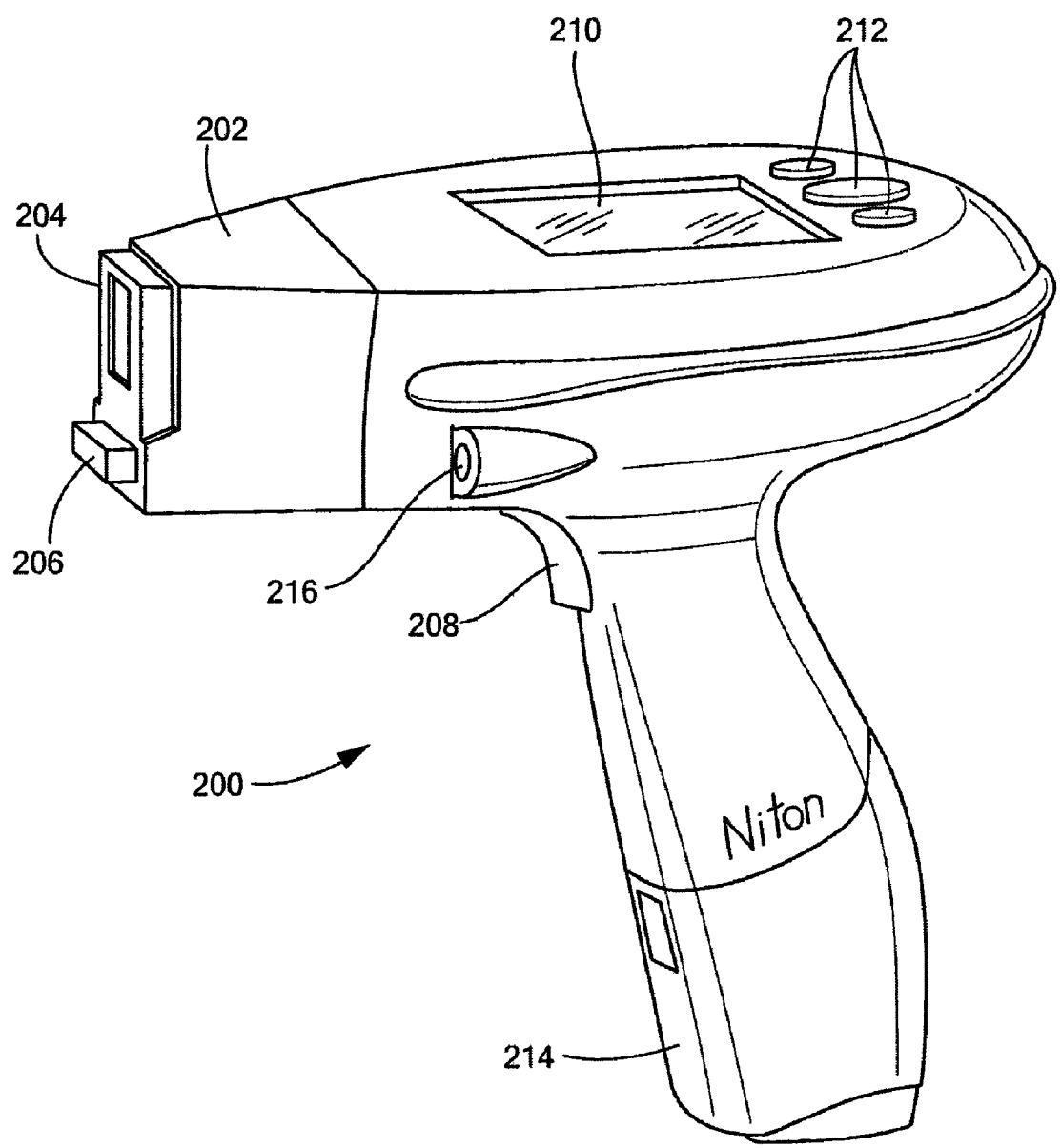
FIG. 2 is a perspective view of a self-contained, hand-held XRF analyzer, according to one embodiment of the present invention.

FIG. 2 is a perspective view of a self-contained, hand-held XRF analyzer 200, according to one embodiment of the present invention. The analyzer 200 includes: a screen 210 (such as a built-in touchscreen or non-touch-sensitive screen or an attached personal digital assistant (PDA)) for displaying analytical results and images and (optionally) receiving operator inputs; a processor and memory (not shown) for storing instructions and data and for controlling operation of the analyzer 200; operator interface buttons 212; a trigger switch 208 for initiating an analysis; and a detachable rechargeable battery 214 for powering all the electrical components of the analyzer 200.

A snout portion 202 houses a collimated shutter (not visible in FIG. 2, but described in detail below) that enables the analyzer 200 to produce a small x-ray spot on the surface of a sample. In operation, a forward wall 204 of the snout 202 is pressed against a sample. When the forward wall 204 comes in contact with the sample, a spring-loaded, momentary contact switch 206 on the forward wall 204 is depressed by the sample. The switch 206 may act as a safety interlock, preventing emission of x-rays outside the analyzer 200 unless the analyzer is pressed against a sample. In another mode of operation, the analyzer 200 is placed in a stand (not shown), which both holds the sample and depresses the switch 206.

Figure 3:
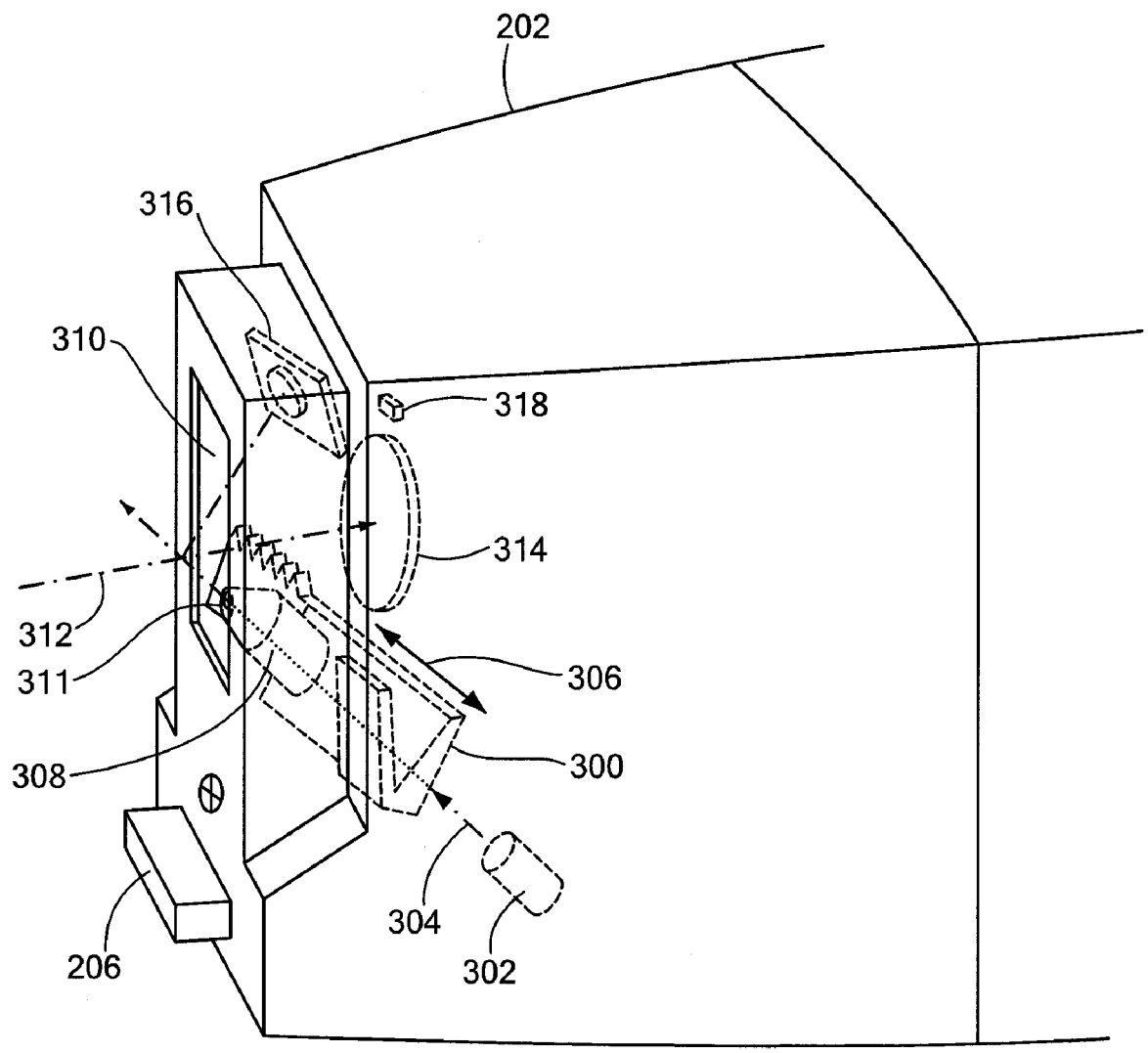
FIG. 3 is a close-up view of a snout of the XRF analyzer of FIG. 2 showing a collimated shutter in a first position, according to one embodiment of the present invention.

FIG. 3 is a close-up view of the snout 202, showing a collimated shutter 300 (mostly in phantom). The collimated shutter 300 includes a tube 308. An x-ray source (shown schematically at 302) produces an x-ray beam 304 directed towards one side (the back) of the collimated shutter 300. As indicated by an arrow 306, the collimated shutter 300 can move laterally or rotationally between at least two positions. In the position illustrated in FIG. 3, the tube 308 is aligned with the x-ray beam 304, between the x-ray source 302 and a window 310, so the x-ray beam may pass through the tube 308, exit the snout 202 via the window 310 and strike a sample (not shown). The end of the tube 308 from which the primary x-rays exit defines a distal exit aperture 311. Fluorescent x-rays 312 from the sample enter the window 310 and strike a detector 314 (shown in phantom). The window 310 may be covered by a thin sheet of x-ray transparent material, such as a polyimide film, to prevent dirt or other contaminants from entering the snout 202 through the window 310. A suitable polyimide film is available under the tradename Kapton from E. I. du Pont de Nemours and Company.

Figure 4:
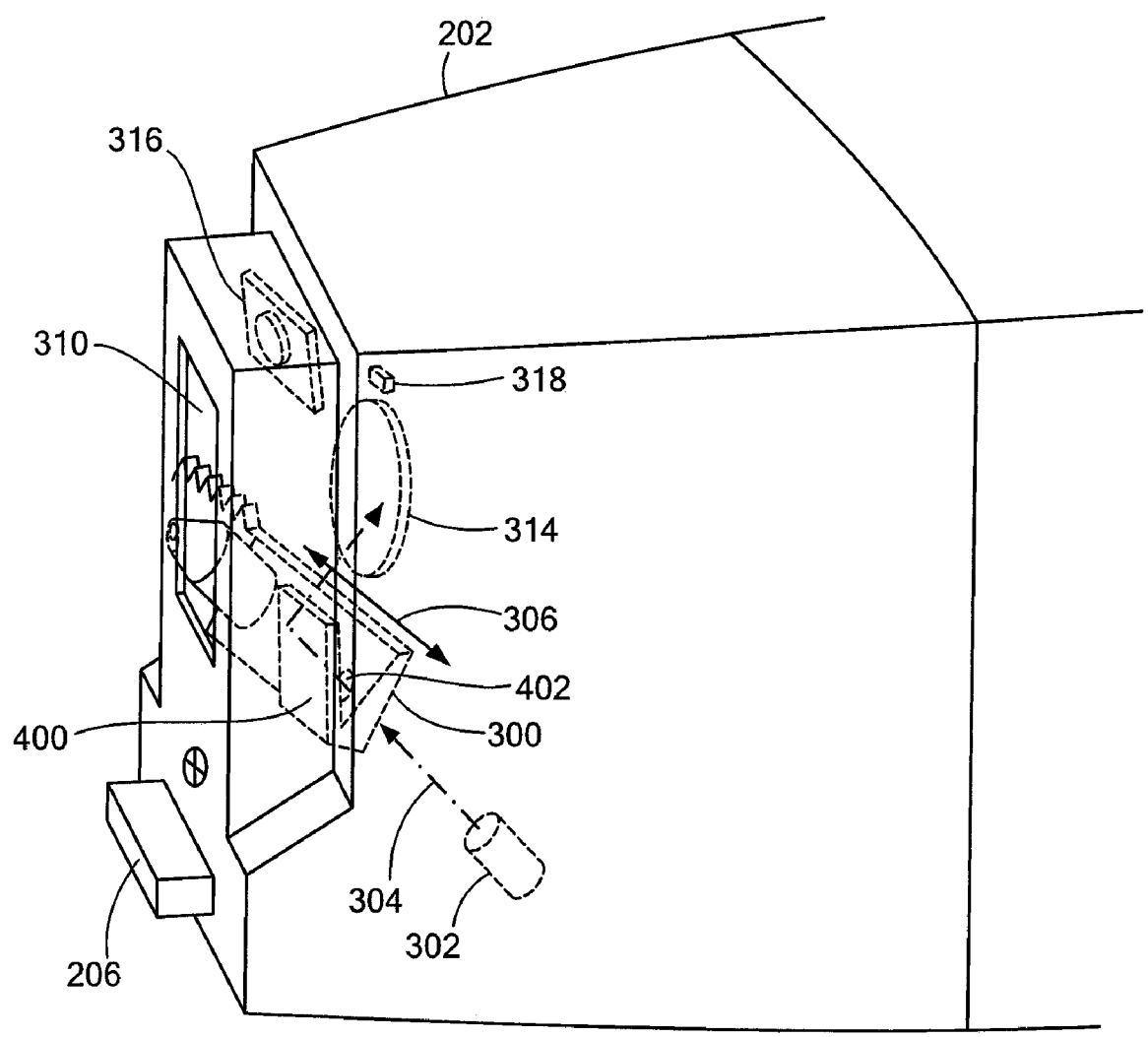
FIG. 4 is a close-up view of the snout of FIG. 2 showing the collimated shutter in another position.

FIG. 4 is a close-up view of the snout 202 showing the collimated shutter 300 in another position, i.e. moved laterally along the arrow 306. In the position illustrated in FIG. 4, the tube 308 is not aligned between the x-ray source 302 and the window 310. The collimated shutter 300 blocks the x-ray beam 304 from exiting the window 310; thus, in this position, the collimated shutter 300 acts as a closed shutter. Instead of exiting the window 310, the x-ray beam 304 passes through a hole 402 and is scattered by an angled portion 400 of the collimated shutter 300. At least some of the scattered x-ray beam reaches the detector 314. In this position of the collimated shutter 300, the detector 314 may be used to calibrate the analyzer 200, with respect to such spectral parameter as the energy scale of the x-ray spectra, the energy resolution of characteristic x -rays, x-ray beam intensity, and the like. Optionally, a calibration sample, such as silver, may be placed on the back side of the angled portion 400 to produce a calibration spectrum.

Figure 5:
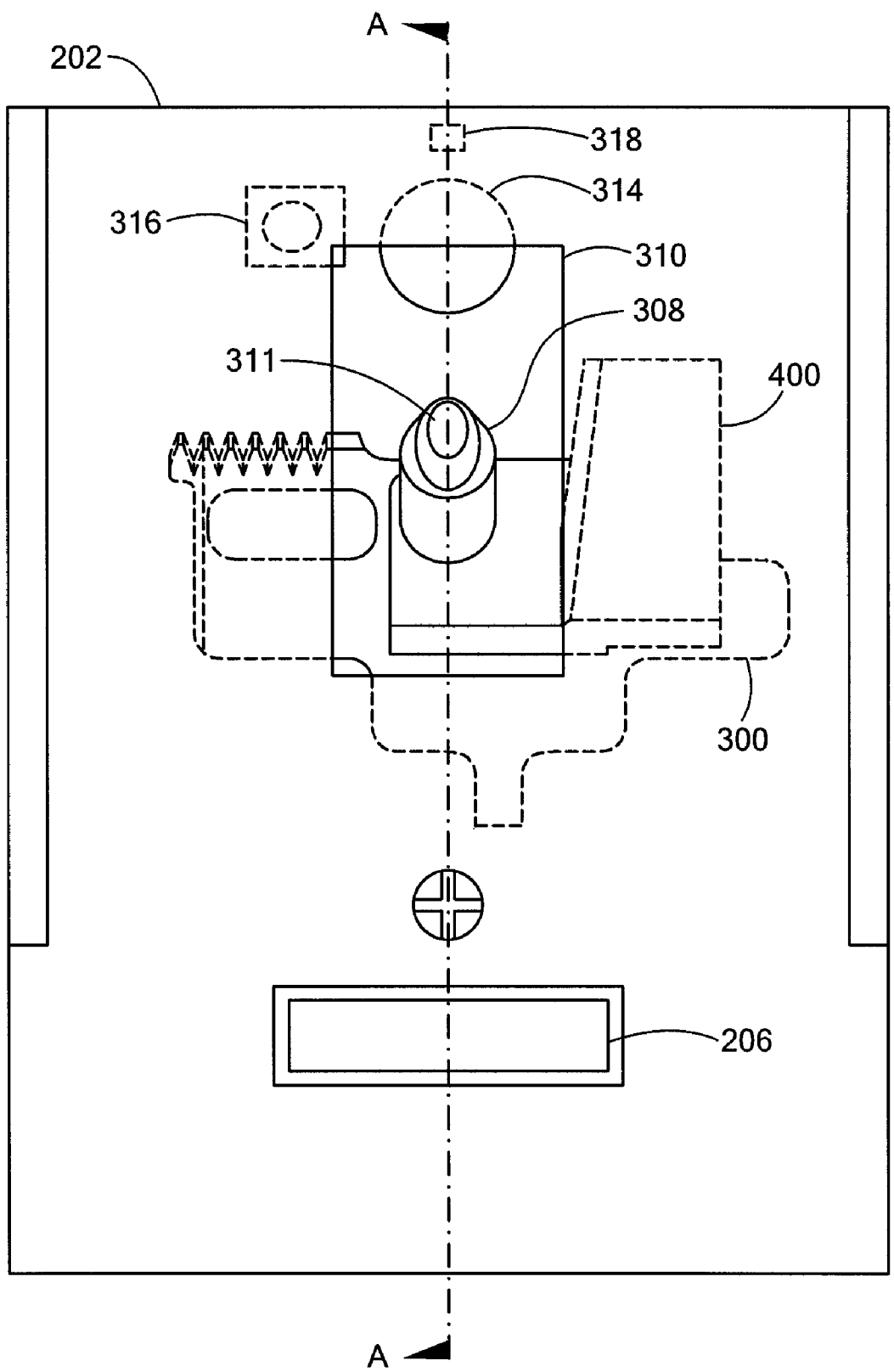
FIG. 5 is a view of the front of the snout of FIG. 2.

FIG. 5 is a view of the front of the snout 202 showing the collimated shutter 300 in the same position as is shown in FIG. 3, i.e., the position that allows the x-ray beam to exit the window 310. As can be seen in FIG. 5, in the position that allows the x-ray beam to pass through the tube 308, the end of the tube 308 closest to the window 310 is approximately centered (left to right) within the window 310. As noted, in the other position (shown in FIG. 4) of the collimated shutter 300, i.e. the position that does not allow the x-ray beam to exit through the window 310, the tube 308 is displaced laterally in the window 310, possibly far enough so that the tube 308 is no longer visible through the window 310.

Figure 6:
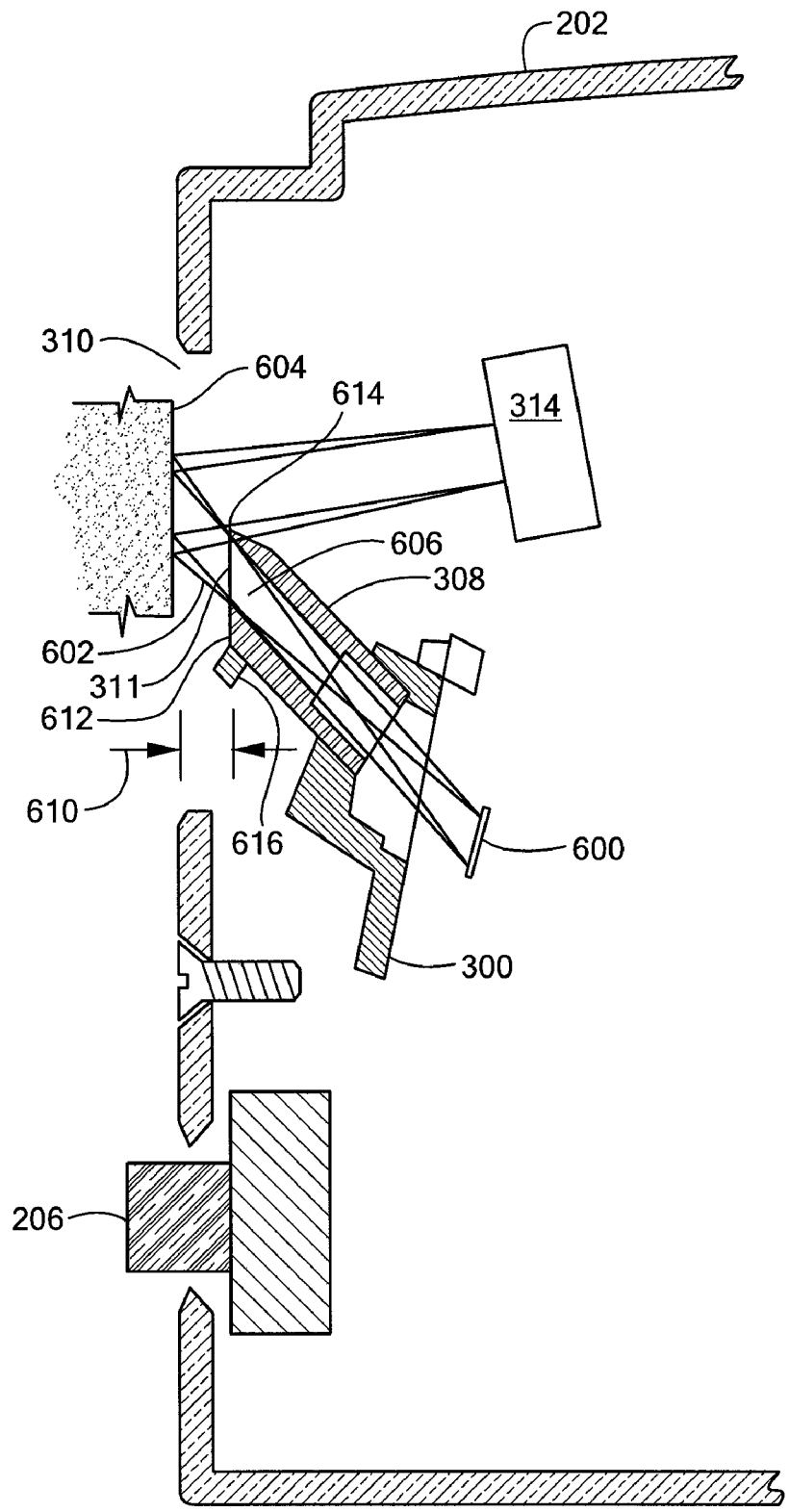
FIG. 6 is a cross-sectional view of the snout of FIG. 5.

FIG. 6 is a cross-sectional view of the snout 202, taken along section line A-A in FIG. 5. An output portion of the primary x-ray source is indicated schematically at 600. This output portion 600 may be an x-ray spot produced on an anode of a miniature x-ray tube (not shown), a part of an encapsulated radioactive material (radioisotope) or any other suitable source of x -rays. Primary filters (not shown) may be introduced between the x-ray source 600 and the collimated shutter 300 to adjust the energy versus intensity spectrum of the primary x-ray beam. If the primary x-ray source is an x-ray tube, the voltage supplied to the x-ray tube may be varied to adjust the energy of the primary x-ray beam.

As shown by ray lines (exemplified by ray line 602), an x-ray beam passes through the tube 308 and exits the snout 202 via the window 310 to illuminate a spot on the surface 604 of the sample. The tube 308 defines a central bore 606, through which the x-ray beam passes. The distal exit aperture 311 is defined where the bore 606 exits the end 612 of the tube closest to the surface 604 of the sample. An infinitesimal primary x-ray spot at 600 would produce no penumbra on the surface 604, whereas a larger primary x-ray spot at 600 produces a penumbra. The size of the penumbra may be limited by close proximity of the distal exit aperture 311 to the surface 604. Thus, the size of the spot on the sample surface 604 is determined primarily by the size of the primary x-ray source spot, the geometry of the central bore 606, notably the size of the distal exit aperture 311, and the distance 610 between the distal exit aperture 311 and the surface 604.

The size of the distal exit aperture 311 is characterized by a transverse dimension, i.e., a dimension of the bore 606 measured along a cross-section of the tube 308 taken perpendicular to the axis of the bore 606, near the end 612 of the tube 308. The cross-sectional shape of the bore 606 may be circular, elliptical, square or any other shape suitable for passing the x-ray beam. If the bore has a circular cross section, the dimension may be a diameter.

The distal exit aperture 311 should be disposed at a distance from the sample no greater than twice the transverse dimension. Preferably, the distal exit aperture 311 should be disposed at a distance from the sample less than, or no greater than, the transverse dimension. If the distal exit aperture 311 and the separation distance 610 are approximately equal, the spot size is approximately equal to, or slightly larger than, the size of the distal exit aperture 311.

In one embodiment, the distal exit aperture 311 is disposed about 2.8 mm from the surface 604 of the sample, and the distal exit aperture 311 has a transverse dimension of about 2.8 mm, thereby producing an approximately 3 mm diameter x-ray spot on the surface 604 of the sample. In other embodiments, the transverse dimension may be between about 0.3 mm and about 8 mm, and the distal exit aperture 311 may be disposed between about 0.3 mm and about 8 mm from the surface 604. Other transverse dimensions and displacements are also possible. The distance between the distal exit aperture 311 and the surface 604 of the sample may depend on the length of the tube 308, which may depend, at least in part due to mechanical strength and rigidity requirements, on the thickness of the wall of the tube 308.

The tube wall thickness may, in turn, depend at least in part on the x-ray flux involved. That is, higher x-ray fluxes may require thicker tube walls. An optimal combination of distance and aperture size may be governed by flux characteristics of the source (such as the intensity (flux) of the beam generated by the source) and feature characteristics of the application (such as how small an area on the sample should be illuminated by the spot). The tube wall thickness may depend on both the energy of the x-rays and their intensities. The energy of the x -rays passing through the tube 308 depends on the voltage applied to the x-ray tube and the filtration of the x-rays. The log of the absorption (I/Io), for a given absorption material, depends linearly on the absorber thickness t, according to I=Io exp($-\mu t$), but it depends on the x-ray energy to the 1.5 to 2 power.

A telescoping collimator (not shown) or other collimator arrangements may be used to produce an adjustable-size spot on the sample within the scope of the present invention.

The shape of the spot on the sample surface 604 is determined primarily by the geometry of the central bore 606, including the shape of the distal exit aperture 311, and the geometric relationship between the plane of the sample surface 604 and the plane of the end 612 of the tube 308. If the plane of the end 612 of the tube 308 were perpendicular to the axis of the bore 606, the projected x-ray spot would be elliptical. However, as discussed below with respect to FIG. 8, the end 612 of the tube 308 may be shaped such that the end 612 is approximately parallel to the surface 604 of the sample. This parallel relationship reduces the eccentricity of the x-ray spot. In addition, an upper edge 614 of the tube 308 may prevent some of the radiation excited in the sample from reaching the detector 314. This cuts off a portion of the x-ray spot and makes the x -ray spot appear more circular, from the perspective of the detector 314. Furthermore, the detector 314 may view the surface 604 of the sample at an oblique angle, further reducing the apparent eccentricity of the x-ray spot.

The bore 606 may have a circular cross-sectional shape to produce a circular or near-circular x-ray spot. However, as noted, the x-ray spot need not be a circle or ellipse. Any shape x-ray spot, such as square, is acceptable in particular applications.

The detector 314 is preferably larger than the x-ray spot, and preferably as large as may be comfortably accommodated within space constraints of the housing and other components in the analyzer. The detector 314 may, if necessary, be cooled to reduce noise, such as "dark current." Conventional thermoelectric or any other suitable cooling mechanism may be used.

Figure 7A:
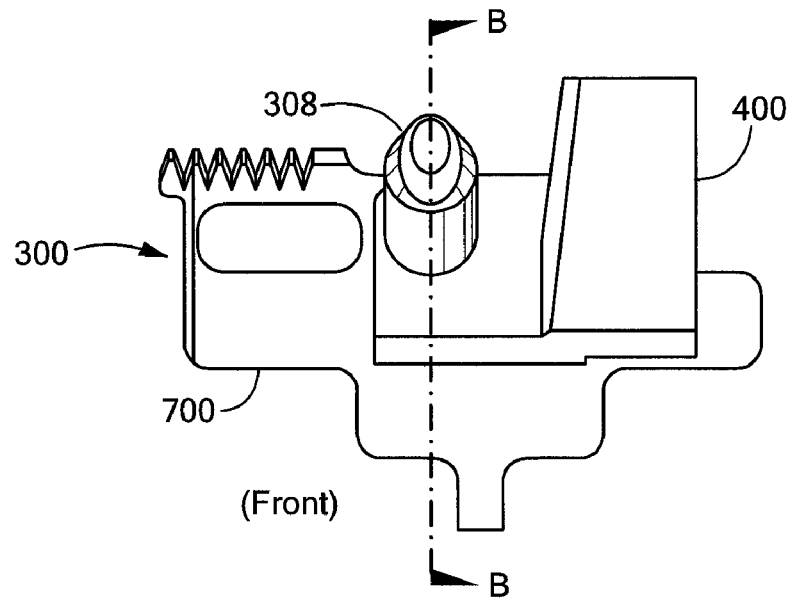
FIGS. 7A, 7B and 7C contain front, bottom and back views, respectively, of the collimated shutter of FIGS. 3-5.
Figure 7B:
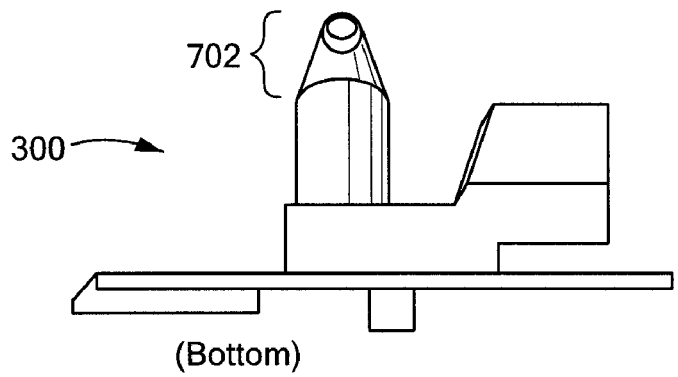
Figure 7C:
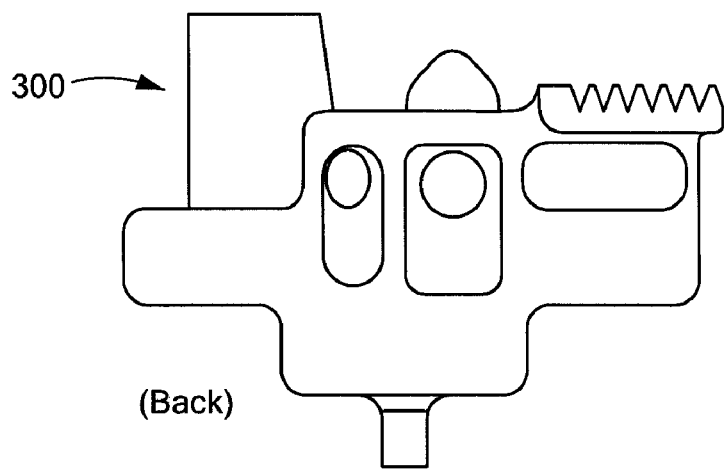
Figure 8:
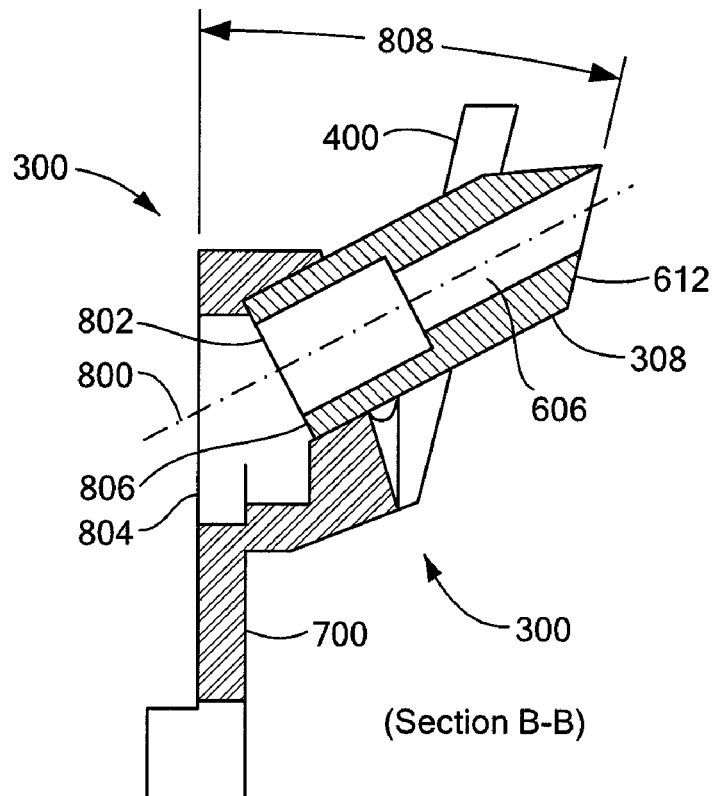
FIG. 8 is a cross-sectional view of the collimated shutter of FIGS. 7A-C.

FIGS. 7A-C contain front, bottom and back views, respectively, of the collimated shutter 300, and FIG. 8 is a cross-sectional view of the collimated shutter taken along section line B-B of FIG. 7A. The collimated shutter 300 includes a shuttle 700, as well as the tube 308 and the angled portion 400 discussed above. The tube 308 is secured to the shuttle 700, such as in a bore. The tube 308 may be secured in the bore by press fitting the tube 308 in the bore, or by a suitable adhesive such as Loctite adhesive (available from Henkel Corp., Rocky Hill, Conn.), or by threading the tube 308 into the bore of the shuttle 700 or by any other suitable mechanism. The angled portion 400 may be formed as part of the shuttle 700, or the angled portion 400 may be attached to the shuttle 700, such as by a suitable adhesive or by welding.

The shuttle 700, the tube 308 and angled portion 400 are preferably made of an x-ray opaque material, such as a tungsten alloy or sintered mixture. Suitable materials include tungsten alloys or mixtures that include about 90% tungsten. Such materials are available under the tradenames Hevimet and Densalloy. Lower percentages of tungsten may be used if the wall thickness of the tube 308 and thicknesses of portions of the shuttle 700 and angled portion 400 are increased sufficiently to block the x-rays. Tungsten may be alloyed with nickel, copper, chrome or other materials to improve its machinability. Other suitable materials for the collimated shutter 300 include lead, tantalum or other elements with atomic numbers, typically greater than 45. Steel or another material may be lined or clad with lead to produce the collimated shutter 300 or portions thereof. The shuttle 700, the tube 308 and angled portion 400, or portions thereof, may be machined from a solid piece of material or may be made using powder metallurgy technology.

The shuttle 700, the tube 308 and angled portion 400, or portions thereof, may also be injection molded as one or more pieces. In one such embodiment, a polymer filled with tungsten or lead powder is used to injection mold the collimated shutter 300 as a single piece.

As noted, and as visible in FIG. 8, the collimated shutter 300 defines a central bore 606 along an axis 800 that passes through the tube 308. As can be seen in FIGS. 6 and 8, the central bore 606 is stepped, i.e., the bore 606 is larger at the end 802 of the tube 308 where the x-rays enter the tube 308 than at the end 612 where the x-rays exit the tube 308. The shuttle 700 defines a yet larger opening 804 where the x-rays enter the shuttle 700 from the primary x-ray source. Collectively, the tube 308 and the opening 804 in the shuttle 700 form a collimator for the primary x-ray beam. To facilitate machining, the collimator may be stepped, as exemplified by the stepped portion of the bore through the tube 308 and by a step 806 formed by the tube 308, where it joins the shuttle 700. However, a conical, tapered or other shaped passage through the collimator is acceptable.

The end 612 of the tube 308 is preferably approximately parallel to the surface 604 of the sample, making the distal exit aperture 311 also approximately parallel to the surface of 604 of the sample. Thus, an angle 808 is selected, such that the end 612 of the tube 308 is approximately parallel to the surface 604 of the sample.

The larger opening 804 at the x-ray source end of the collimator allows for some imprecision in the size or location of the x-ray emitting spot on the x-ray tube anode or other primary x-ray source. However, the proximity (i.e., the small distance 610 (FIG. 6)) of the end 612 of the tube 308 to the surface 604 of the sample minimizes the possible effect of parallax.

The proximity of the end 612 of the tube 308 to the surface 604 may cause portions of the tube 308 to block some of the fluorescent x-rays from reaching the detector 314, i.e. portions of the tube 308 may "shade" the detector 314. Furthermore, fluorescent x-rays from the sample, as well as primary x-rays reflected from the surface 604 of the sample, may react with portions of the tube 308 to produce spurious fluorescent or reflected x-rays from the tube 308. These spurious x-rays may reach the detector 314 and contribute noise to the analysis system. To reduce the amount of shading of the detector 314, and to reduce the likelihood of generating spurious x-rays, an end portion 702 (FIG. 7B, bottom view) of the outside of the tube 308 is tapered. Optionally or alternatively, the outside of the tube may be stepped or given another symmetric or asymmetric shape. Thus, as best seen in the cross-sectional view in FIG. 8, the wall thickness near the end of the tube 308 is reduced, although this reduction may be asymmetric about the circumference of the tube. Shaping the end portion of the tube 308 as described reduces the amount of tube 308 material in the path of fluorescent and reflected primary x-rays from the sample. Nevertheless, a portion of the tube 308 may remain within the field of view of the detector 314.

Figure 10:
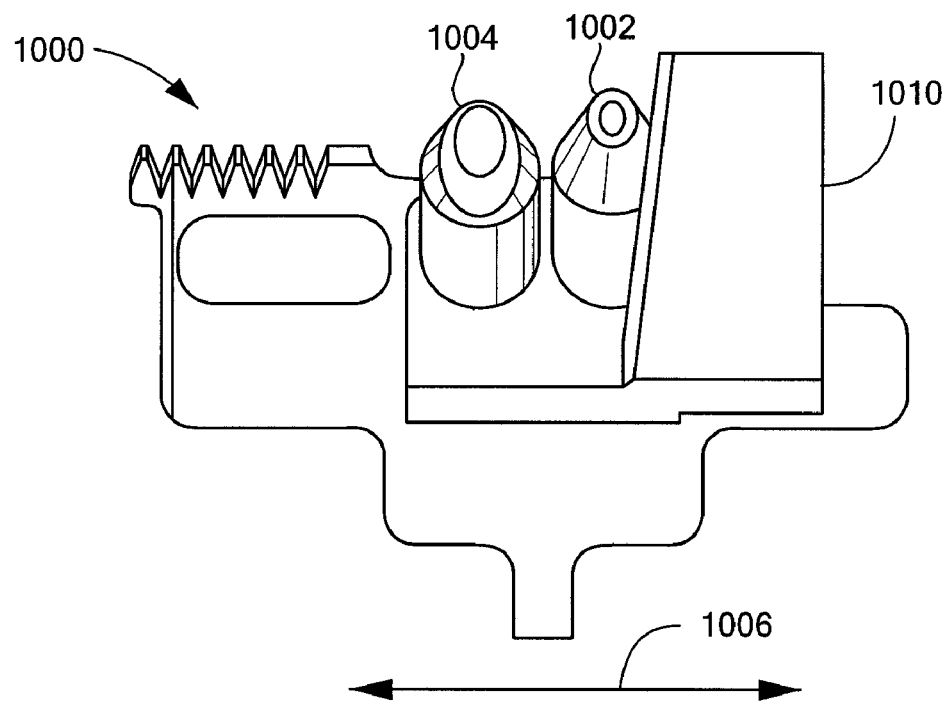
FIG. 10 is a front view of a collimated shutter, according to another embodiment of the present invention.

FIG. 10 is a front view of another embodiment of a collimated shutter 1000. The collimated shutter 1000 includes two tubes 1002 and 1004. Each of the tubes 1002 and 1004 has a different diameter central bore (and, thus, a different distal exit aperture dimension) and/or a different length. The tubes maybe arranged in any order of diameters or lengths.

The collimated shutter 1000 may be translated laterally, as indicated by an arrow 1006, such as by a gear rack 1008 and a spur gear (not shown) or by any other suitable mechanism, into one of at least three positions. In one position, the primary x-ray beam is prevented from reaching the sample, and an angled portion 1010 reflects the primary x-ray beam into the detector, as previously discussed. In the second position, one of the tubes (1002 or 1004) is aligned between the primary x-ray source and the sample. In the third position, the other tube is aligned between the primary x-ray source and the sample.

Thus, the collimated shutter 1000 includes two collimators defined, respectively, by the two tubes 1002 and 1004. Each of the tubes 1002 and 1004 produces a different diameter x-ray spot on a sample. Preferably, the longer tube has the smaller central bore diameter (at the end of the tube closest to the sample), so the tube that produces the smaller primary x-ray spot is closer to the sample surface than the tube that produces the larger spot. In one embodiment, the two tubes 1002 and 1004 have central bore diameters of about 3 mm and about 8 mm, respectively, and the lengths of the tubes 1002 and 1004 are such that, when each tube is in position to allow the x-ray beam to illuminate a spot on the sample, the end of the tube is about 3 mm or about 8 mm, respectively, from the surface of the sample. Other pairs of bore diameters and lengths may be used to produce other sizes of x-ray spots. Other embodiments may have other numbers of tubes and, thus, produce other numbers of diameters of x-ray spots.

Figure 11:
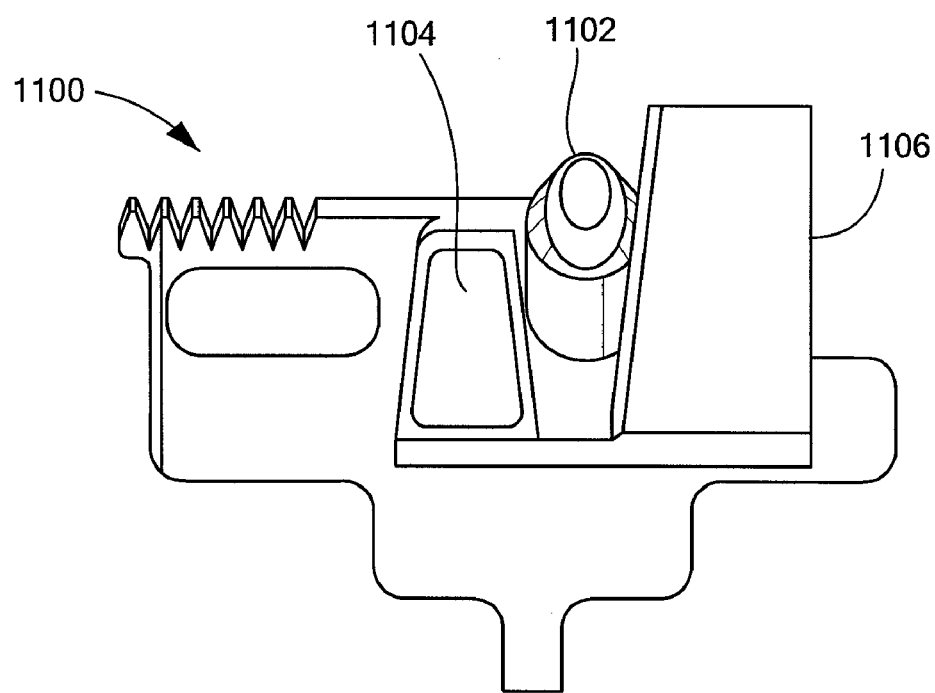
FIG. 11 is a front view of a collimated shutter, according to yet another embodiment of the present invention.

FIG. 11 is a front view of yet another embodiment of a collimated shutter 1100. The collimated shutter 1100 includes a tube 1102 and a large hole 1104. The large hole 1104 is similar to the hole 906 described above, with respect to FIG. 9. The collimated shutter 1100 may be translated laterally into one of at least three positions, as discussed above. In one position, the primary x-ray beam is prevented from reaching the sample, and an angled portion 1106 reflects the primary x-ray beam into the detector, as previously discussed. In the second position, the tube 1102 is aligned between the primary x-ray source and the sample. In the third position, the hole 1104 is aligned between the primary x-ray source and the sample. The tube 1102 and the hole 1104 produce different size primary x-ray spots on the sample. The dimensions of the tube 1102 may be selected to produce a small spot, such as a spot having a diameter of between about 0.3 mm and about 8 mm, as discussed above. The dimensions of the hole 1104 may be as in the prior art to produce an x-ray spot having a diameter of about 1 cm. Larger or smaller spots may, of course, be produced by varying the dimensions of the tube 1102 or the hole 1104.

Various embodiments of collimated shutters have been described as including one or more tubes. Each of these tubes forms at least a part of a collimator. Although tubular collimators with circular inside cross-sections are preferred due to the relative ease of manufacturing such shapes, other shapes (such as square, oval or triangular cross-sections) are acceptable. Furthermore, as noted, the inside walls of a collimator may be stepped or smooth, or the walls may have other types of transitions between sections having different inside diameters or shapes.

Although collimated shutters have been described as being movable laterally to interpose either a tubular collimator (or one of several tubular collimators) or a reflecting surface between a primary x-ray source and a sample, other motions, such as a circular motion, and other mechanisms, such as a turret, may be used to selectively move a desired collimator or reflecting surface into place between the x-ray source and the sample.

Although analyzers have been described as including collimated shutters, an analyzer according to the present invention may include a tubular collimator that does not move into and out of position to permit a primary x-ray beam to illuminate a spot on a sample. In other words, the tubular collimator may be fixed in place. Electric power to an x-ray tube may be interrupted, such as under the control of a processor, to prevent x-rays from exiting the analyzer window. Alternatively or in addition, a shutter may be interposed between the primary x-ray source and the collimator or the sample to interrupt the x-ray beam and, optionally, reflect the x-ray beam to the detector. Such a shutter may include a solid surface, an iris or any other suitable mechanical, electronic, chemical or electrochemical (such as polymer dispersed liquid crystal, which changes x-ray opacity in response to an applied electric field) mechanism for selectively blocking the x-ray beam. Thus, the shutter may be separate from the tubular collimator.

Detector Collimator

As noted, fluorescent x-rays from a sample, as well as primary x-rays reflected from the surface 604 or from material slightly below the surface 604 of the sample, may react with portions of the tube 308 to produce spurious fluorescent or reflected x-rays from the tube 308. In addition, fluorescent or scattered primary x-rays from the sample may strike other portions of the sample or the analyzer and induce spurious secondary fluorescence. These spurious x-rays may reach the detector 314 and contribute noise to the analysis system.

Figure 12:
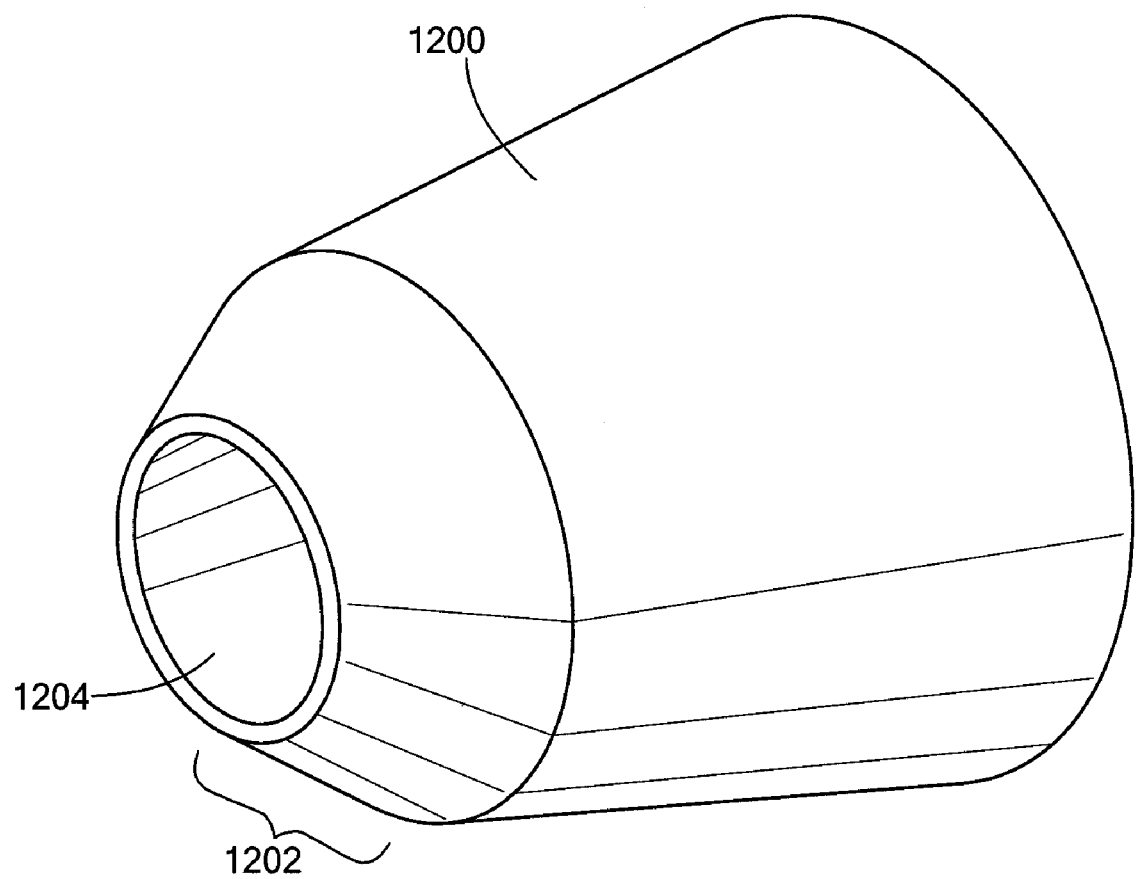
FIG. 12 is a perspective view of a detector collimator, according to one embodiment of the present invention.
Figure 13:
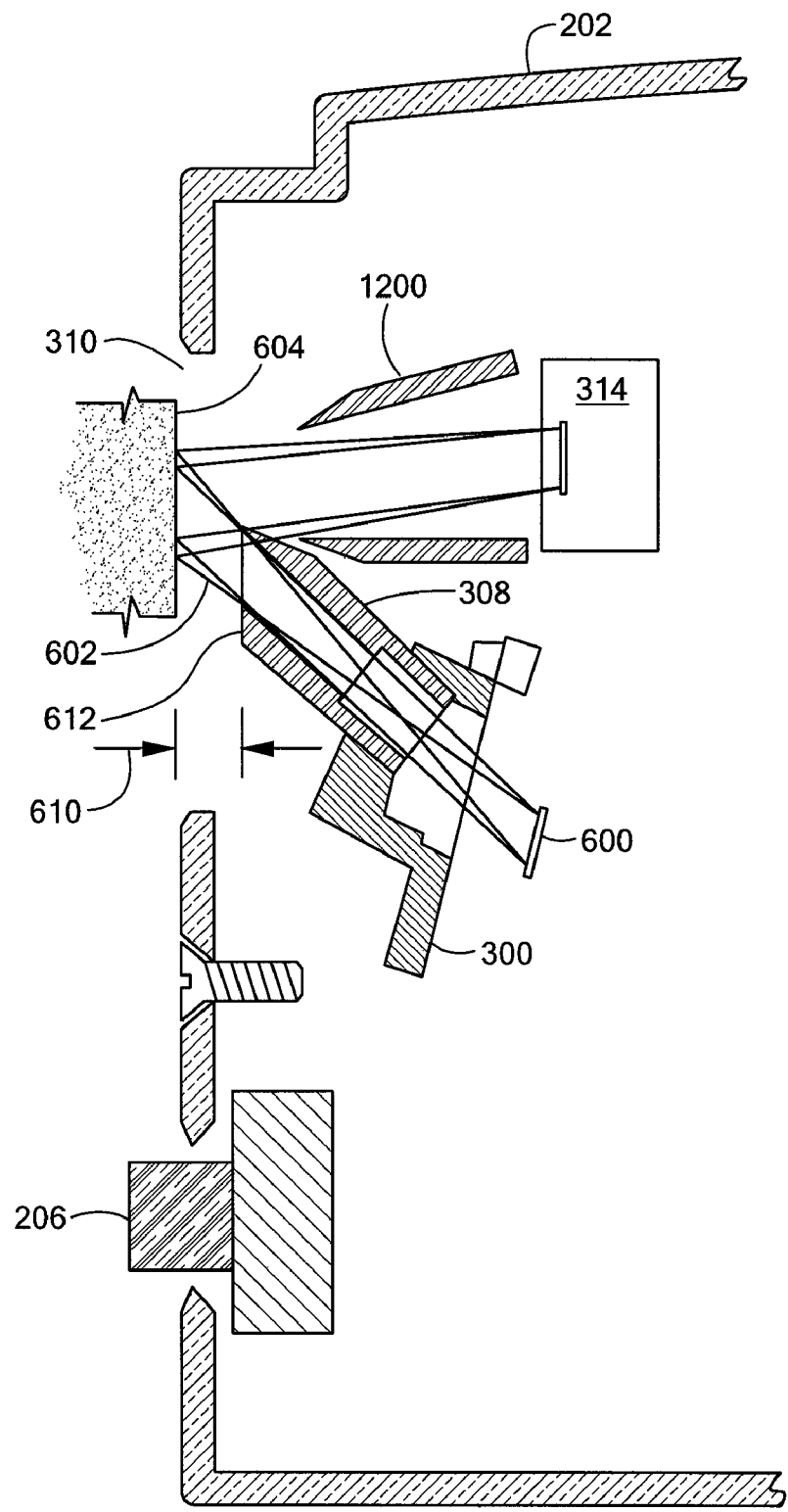
FIG. 13 is a cross-sectional view through the snout of an XRF analyzer that includes the detector collimator of FIG. 12.
Figure 14:
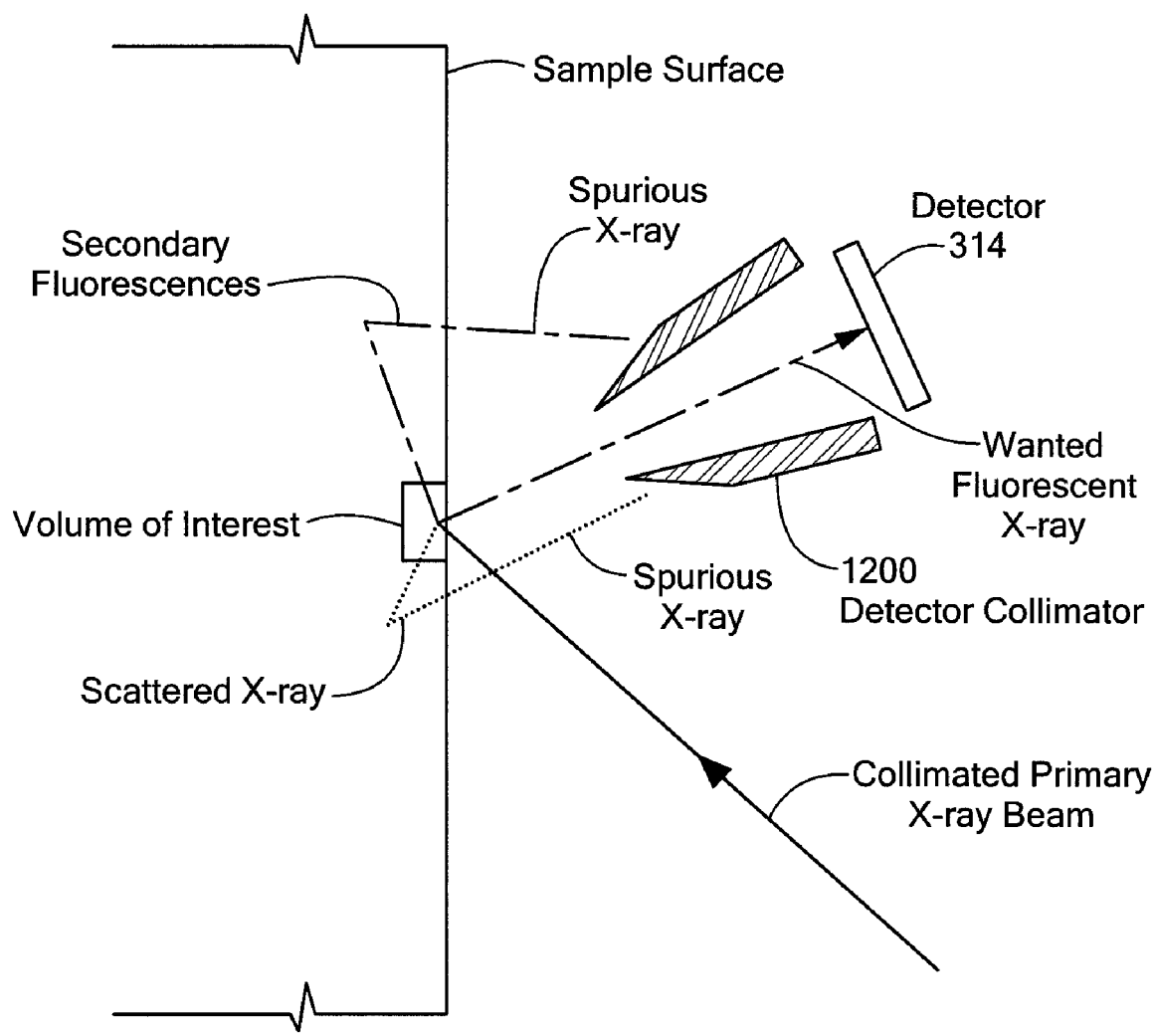
FIG. 14 is a schematic diagram of the detector collimator of FIG. 13 in use.

These and other spurious x-rays may be prevented from reaching the detector 314 by a detector collimator. FIG. 12 is a perspective view of a detector collimator 1200, according to one embodiment of the present invention. FIG. 13 is a cross-sectional view through the snout 202 of an XRF analyzer that includes the detector collimator 1200 of FIG. 12. As best seen in FIG. 12, a portion 1202 of the end of the detector collimator 1200 closest to the sample may be tapered, as discussed above with respect to the tube 308. The inside walls, as seen in a cross-section of the detector collimator 1200, may be parallel or non-parallel, i.e. the detector collimator 1200 may have an overall taper. Furthermore, the inside walls of the detector collimator 1200 may be smooth or stepped or they may have some other shape. The detector collimator 1200 should be made of an x-ray opaque material, as discussed above with respect to the collimated shutter 300. Optionally, the inside walls of the detector collimator 1200 may be covered or clad with one or more layers of material(s) that reduce the intensity of spurious radiation scattered from, or generated in, the walls of the detector collimator 1200. As shown schematically in FIG. 14, the detector collimator 1200 prevents many of the spurious x-rays from reaching the detector 314.

The entrance 1204 (FIG. 12) to the detector collimator, i.e., the opening closest to the surface 604 of the sample, should be no larger than the effective spot size, as seen by the detector 314 on sample surface. The entrance 1204 may, however, be smaller than the effective spot size.

Figure 15:
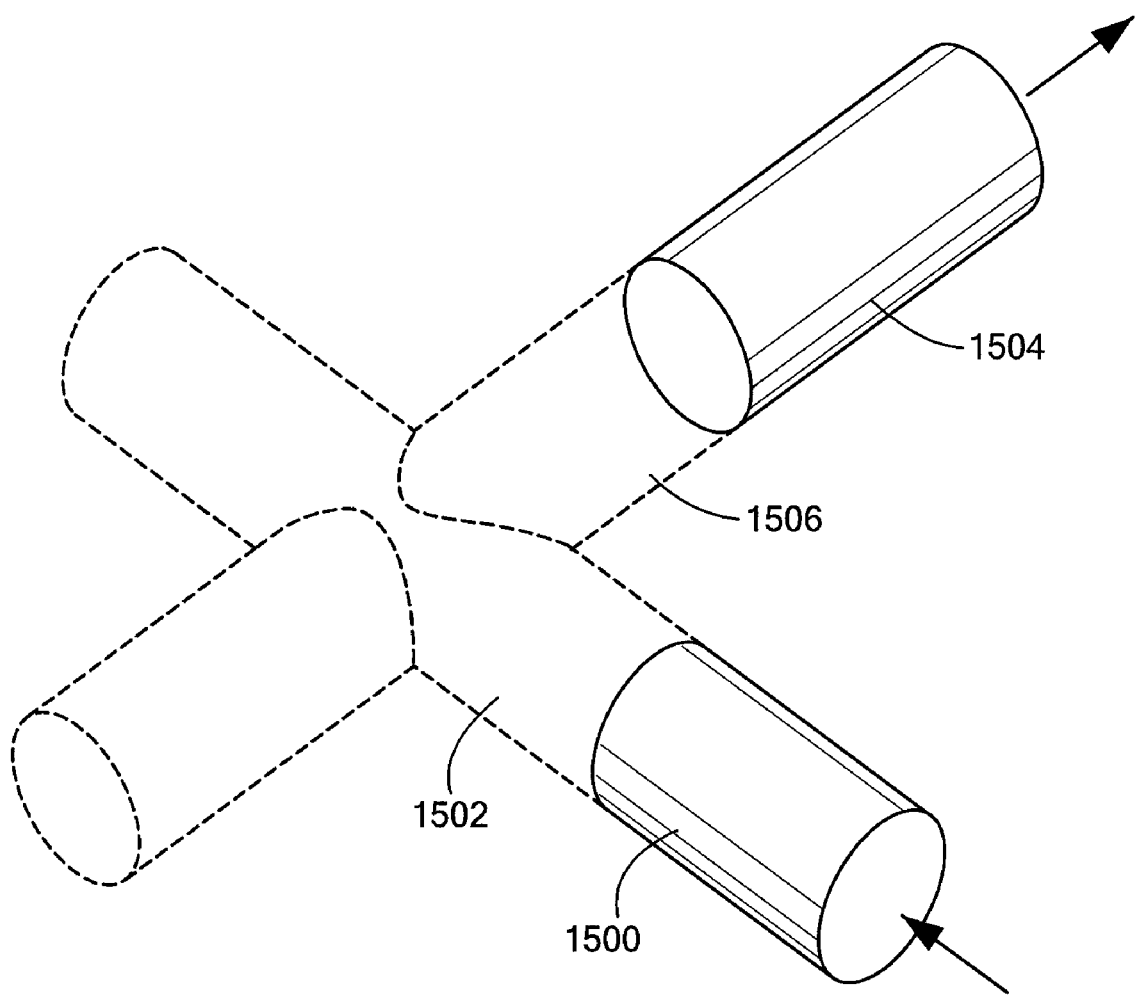
FIG. 15 is a schematic diagram of a source collimator and a detector collimator in use, according to one embodiment of the present invention.

As shown schematically in FIG. 15, a source collimator 1500 defines a cylindrical or slightly conical field of illumination 1502, and a detector collimator 1504 defines a cylindrical or slightly conical field of view 1506. Using both the source collimator 1500 and the detector collimator 1504, the detector receives x-rays emanating from only a volume defined by the intersection of the two fields 1502 and 1506. Thus, by appropriately orienting and sizing the two collimators 1500 and 1504, the size and location of a sample of interest at or slightly below the surface of the sample may be specified, and scattered or fluorescent x-rays from other portions of the sample or from elsewhere may be prevented from reaching the detector 314.

Digital Imaging of Tested Sample

Aiming a hand-held XRF analyzer that utilizes a small x-ray spot can be challenging, particularly because the front wall of the snout covers an area of the sample that is considerably larger than the spot. Some embodiments of the present invention include a digital camera inside the snout to facilitate aiming the analyzer. An image produced by the digital camera may be displayed on the touchscreen 210 (FIG. 2). Optionally, a reticule that indicates where the x-ray spot is, or would be, is also shown on the touchscreen 210. Alternatively or in addition, the image may be displayed on a remote screen, such as a screen attached to a computer. The analyzer may include a port by which the analyzer may send the image to the remote display over a wired or wireless link. Optionally, the image may be digitally zoomed or otherwise reoriented to the center or another selected portion of the camera's image plane. Commands to zoom, pan, tilt, etc. the image may be entered by a user via the touchscreen 210 or the operator interface buttons 212.

As shown in FIG. 3, a digital camera 316, such as a single-chip, lensed digital camera, is positioned within the snout 202 and oriented towards the portion of the sample where the fluorescent x-rays 312 are generated. A suitable camera is available from Micron Technology, Inc., Boise, ID under part number MT9V112, and a suitable lens is available from Edmunds Optics, Inc., Barrington, N.J. under part number NT47-725. Appropriate software to process signals from the digital camera 316 is available under the tradename Direct-Show API from Microsoft, Redmond, Wash.

A visible light source 318, such as a surface-mounted LED, is mounted above the detector 314 to illuminate the surface of the sample visible through the window 310. If a colored film, such as an orange Kapton polyimide film, covers the window 310, an LED that produces a similar color light should be selected. Otherwise, other colors of light produced by the LED will not be efficiently transmitted through the colored film, and these other colors of light will not materially contribute to an image produced by the camera 316. Consequently, energy consumed by the LED to produce the other colors of light will be essentially wasted, thereby decreasing the amount of time the analyzer may be operated before the battery 214 must be recharged. Automatic white balance and other conventional color correction algorithms available with single-chip digital cameras or processing software correct for the orange (or other color) tint of the image, thus producing a naturally-colored image for display on the touchscreen 210, on an external monitor (not shown) or when the image is stored in a memory.

Ideally, the camera 316 should be mounted so the camera's image plane is parallel to the surface of the sample, and so the camera is centered over the x-ray spot. However, as can be seen in FIG. 5, depending on the position of the shuttle 300, the tube 308 or the angled portion 400 may block the camera's view. In addition, there may be insufficient space to mount the camera in such an ideal location. The camera may, therefore, be mounted off-center, relative to the x-ray spot and angled, relative to a line normal to the sample surface. Such a position and orientation of the camera result in a somewhat distorted image that is, nonetheless, useful for aiming the analyzer. Optionally, the processor may execute a flattening algorithm to remove most or all of the distortion before displaying the corrected image on the touchscreen 210 or elsewhere. The flattening algorithm may employ a homography matrix or other well-known methods for flattening an image.

Facilitating Aiming an Analyzer

Although an image produced by a camera within the snout of an analyzer may assist a user in aiming an analyzer at a desired location on a sample, most digital cameras are not sensitive to x-rays, thus most such images would not directly show the x-ray spot. Various embodiments are disclosed for assisting the user in aiming the analyzer.

Some embodiments of the present invention project a spot of visible light on the sample where the x-ray spot is, or would be, to assist a user in aiming the analyzer. As shown in FIG. 6, a laser diode or LED 616 may be attached to the collimator tube 308 or elsewhere and aimed so a beam produced by the laser diode or LED 616 creates a visible spot on a portion of the surface 604 of the sample where the x-ray spot is or would be. The visible spot need not be the same size as the x-ray spot. The visible light source may be pulsed, so the visible spot blinks to facilitate viewing features on the surface of the sample.

Figure 17:
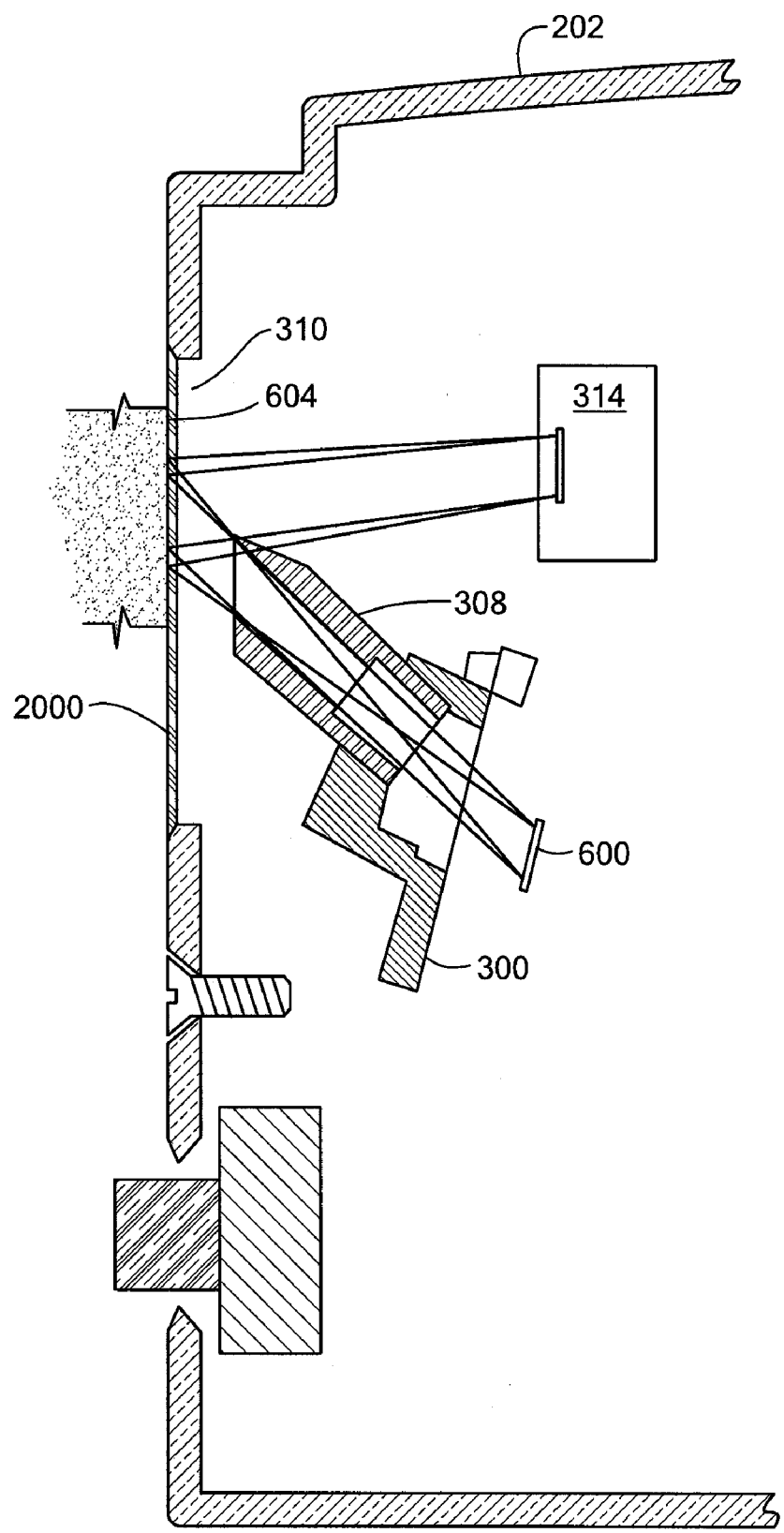
FIG. 17 is a cross-sectional view of a snout that includes a fluorescent screen in or near a window of the snout, according to one embodiment of the present invention.

As shown in FIG. 17, some embodiments of the present invention include a fluorescent screen 2000 in or near the window 310 of the snout 202, so the primary x-ray beam produces a visible spot that may be imaged by the camera (not shown in FIG. 17). The fluorescent screen may be made of any suitable material that produces visible light when illuminated by x-rays.

Some embodiments of the present invention add a reticule that indicates where the x-ray spot is, or would be, to the image produced by the camera. A reticule may be a cross-hair, hash mark or other shape or combination of shapes that assist the user in aiming an analyzer at a location of interest on a sample. The reticule may include a circle or other shape that approximates the shape, size and location of an outline of the x-ray spot. The term "reticule" means any shape or shapes that are added to the image produced by the camera to facilitate aiming the analyzer. The term reticule is not limited to cross hairs, concentric circles, fine dots and the like, as may be the case when the term is used in other contexts, such as microscopes and other optical instruments.

Figure 16:
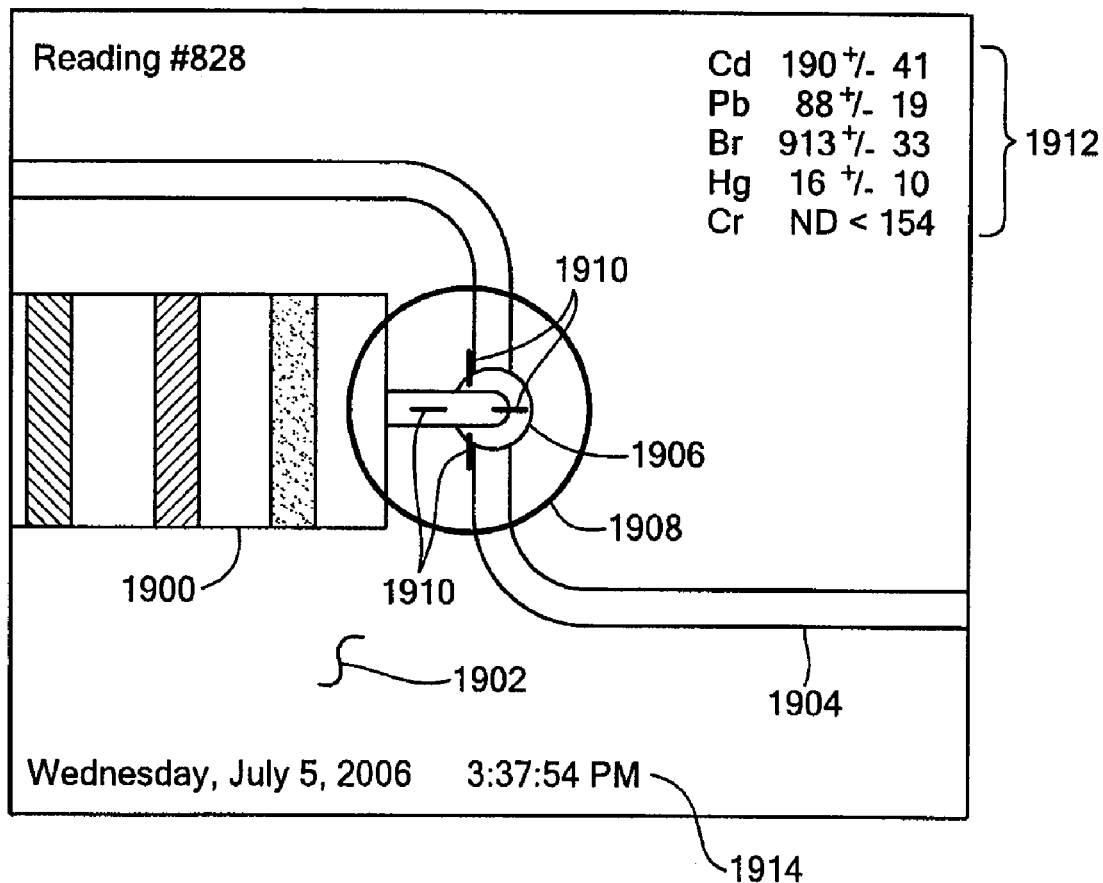
FIG. 16 is an exemplary image produced by a camera in the snout of an analyzer, according to one embodiment of the present invention.

FIG. 16 is an exemplary image produced by a camera in the snout of an analyzer. The image includes an electrical component 1900 (such as a resistor) soldered to a printed circuit board 1902. The image also includes a circuit trace 1904 and a solder joint 1906 between a lead of the component 1900 and the trace 1904. A reticule circle 1908 is generated by the analyzer and included in the image. An optional reticule cross hair 1910 may also be generated by the analyzer and included in the image to indicate the center of the x-ray spot.

A color may be dynamically chosen for all or a portion of the reticule to ensure the reticule is visible against a background. In one embodiment, a color is dynamically chosen for the reticule cross hair 1910, based on the color of underlying pixels, so the cross hair 1910 is always visible, regardless of the color of the underlying pixels. In one embodiment, the color of the cross hair 1910 is dynamically chosen to be one of two values (referred to as a light color and a dark color), such as black and white, as follows. An average brightness is calculated for the pixels that are to be occupied by the cross hair 1910. The brightness of a pixel (for example, a value between 0 and 255) is defined as one third of the sum of the pixel's red, green and blue color intensities. If the average pixel brightness is less than the difference between a predetermined threshold value (T) and a predetermined hysteresis value (H) (i.e., less than T−H), and the cross hair 1910 is currently drawn in a dark color, the color of the cross hair 1910 is changed to the light color. On the other hand, if the average pixel brightness is greater than T+H, and the crosshair 1910 is currently drawn in the light color, the color of the crosshair 1910 is changed to the dark color. Otherwise, the color remains unchanged. Threshold and hysteresis values of T=175 and H=10 have been found to provide satisfactory results, which prevent the crosshair from unduly flickering between colors, such as due to image noise. Other values of T and H may be used.

A color may be dynamically chosen for all or a portion of the reticule to make it translucent. In one embodiment, a base color (such as reddish orange) is chosen for the reticule circle 1908. The color of each pixel of the circle 1908 is then dynamically modified, based on the color of an underlying pixel, so text or other features on the surface of the sample are not completely obscured by the circle 1908. For each pixel that is to be overlaid by a translucent reticule, the pixel's red, green and blue intensities are each modified by multiplying the intensity by a number K (0<K<1) to simulate partial light transmission. The red, green and blue intensities of the reticule's base color are scaled (multiplied) by 1-K and added to the modified red, green and blue intensities, respectively, of the underlying pixel. A value of K=0.4 has been found to provide satisfactory results; however, other values of K may be used.

Reticule Calibration Target

The location of a reticule within an image produced by an analyzer should accurately reflect the location of the x-ray spot. Manufacturing tolerances may, however, cause analyzer-to-analyzer variations in the location of the x-ray spot on the surface of a sample. In addition, through use of an analyzer, as a result of replacing the x-ray source or due to jarring of the analyzer, such as during shipment, the location of the x-ray spot on the surface of the sample may change. It may, therefore, be necessary or desirable to calibrate or re-calibrate the location of the reticule, such as during manufacturing, after replacement of the x-ray source or during analyzer maintenance. Various methods and apparatus are disclosed for calibrating or re-calibrating (collectively hereinafter referred to simply as calibrating) the location, shape and/or size of a reticule. In some embodiments, a calibration target may be used to facilitate calibrating the reticule.

Figure 18:
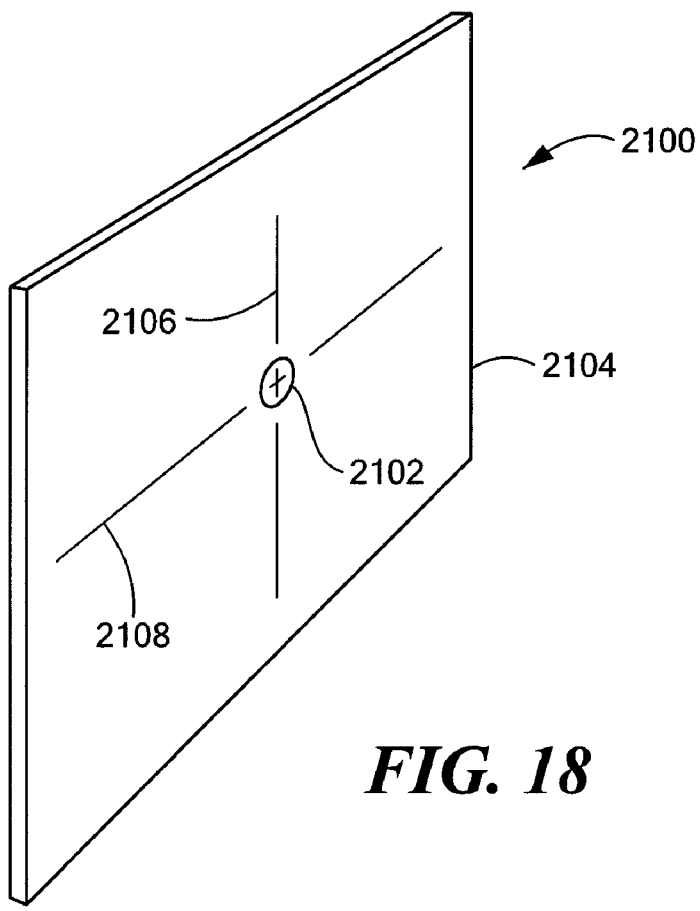
FIG. 18 is a perspective view of a reticule calibration target, according to one embodiment of the present invention.

FIG. 18 is a perspective view of a reticule calibration target 2100. The calibration target 2100 includes a plug 2102 embedded in a sheet 2104 or adhered to the surface of the sheet 2104. The plug 2102 should be relatively small, i.e., on the order of the size of the x-ray spot. The plug 2102 is made of a different material than the sheet 2104. In one embodiment, the plug has a diameter of about 3.5 mm, a thickness of about 10 mil and is made of copper, and the sheet may be made of titanium, a solid polymer or a solid polymer with titanium. In one embodiment, the sheet is about 12 mm-thick, about 31 mm in diameter, and includes a solid polymer containing 5% titanium as an oxide. At least one of the materials of the calibration target 2100 should be detectable by the analyzer. Optionally, the calibration target 2100 also includes indicia 2106 and 2108 in the form of crosshairs or a spot centered on the plug 2102. Although the calibration sheet 2100 shown in FIG. 18 is square, the calibration target may be other shapes, such as a circle.

In use, the front wall of the snout of an analyzer is pressed against the calibration target 2100, such that the window of the snout covers the plug 2102. Measurements are taken, and the analyzer is moved (relative to the calibration target 2100) after each measurement, until a maximum reading (within some error tolerance) for the material of the plug 2102 is taken. At this point, the x-ray spot can be assumed to be centered on the plug 2102, and the reticule may be made to correspond to the location of the plug 2102. An image of the plug 2102 may be displayed on the touchscreen or another display screen, and the location of the reticule may be made to correspond with the location of the plug 2102 in the image. The indicia 2106 and 2108 (or other indicia, not shown) may facilitate aligning the reticule or portions thereof with the center of the plug 2102.

If the materials of the plug 2102 and the sheet 2104 are both detectable by the analyzer, the above-describe procedure may involve alternating taking measurements and moving the analyzer until a maximum reading for the material of the plug 2102 is taken and, simultaneously, a minimum reading for the material of the sheet 2104 is taken.

If the plug 2102 is made of the material that is not detectable by the analyzer, the above-described procedure may be used until a minimum reading for the material of the sheet 2104 is taken. In this regard, the plug 2102 may be replaced by a hole in the sheet 2104.

If a real-time image of the sample under test is available, such as on the touchscreen of the analyzer or another display screen, the distal portion of the tube 308 may be visible in the image. The analyzer may be positioned, relative to the calibration target 2100, such that an imaginary extension of the tube 308 intersects the plug 2102. The reticule may be made to correspond to the location of the plug 2102 in the image. The location of the reticule may be refined as described above or below.

Figure 19:
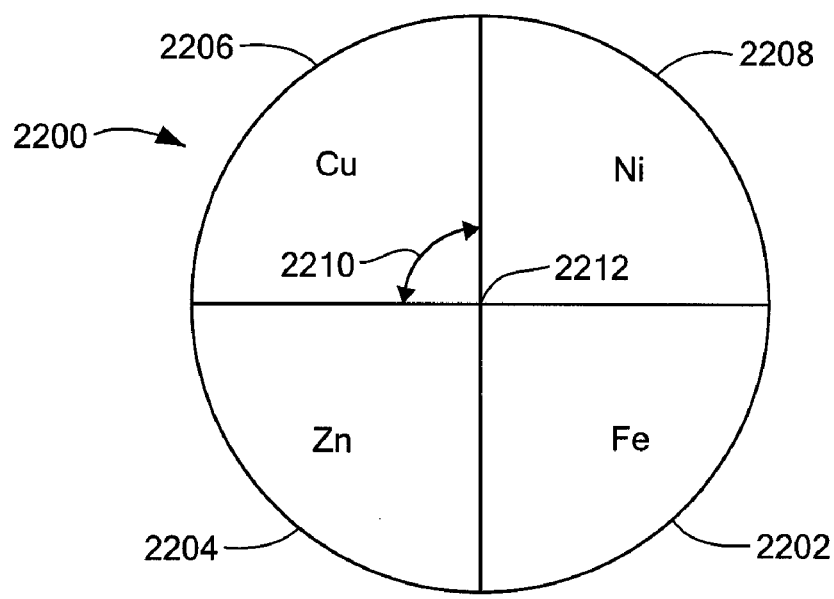
FIG. 19 is a plan view of a reticule calibration target, according to another embodiment of the present invention.

FIG. 19 is a plan view of another reticule calibration target 2200. The calibration target 2200 includes a plurality of pie-shaped sections 2202, 2204, 2206 and 2208, each of which is detectable by the analyzer. As used herein, "pie-shaped" means two adjacent sides of each section form an angle (the "vertex angle"), exemplified by angle 2210.

Although the calibration target 2200 shown in FIG. 19 includes four sections, other numbers of sections may be used; however, each section 2202-2208 is made of a different material. The reticule calibration target 2200 shown in FIG. 19 includes an iron section 2202, a zinc section 2204, a copper section 2206 and a nickel section 2208; however, other combinations of detectable materials may be used. Preferably, all the pie-shaped sections 2202-2208 have identical vertex angles (exemplified by angle 2210) where the pie-shaped sections meet in the center 2212 of the calibration target 2200. However, if unequal vertex angles are used, the calibration algorithm should take into account the expected ratios of materials in the respective sections, based on the respective vertex angles. The sum of the vertex angles of all the sections 2202-2208 is 360 degrees.

In use, the front wall of the snout of an analyzer is pressed against the calibration target 2200, such that the window of the snout covers the center 2212 of the calibration target 2200. Measurements are taken, and analyzer is moved (relative to the calibration target 2200) after each measurement, until a measurement is taken that indicates equal amounts of all the materials of the calibration target 2200. At this point, the x-ray spot may be assumed to be centered on the center 2212 of the calibration target 2200, and the reticule may be made to correspond to the location of the center 2212. The center 2212 may be marked on the calibration target 2200, such as by a dot, crosshairs or other indicia (not shown). Furthermore, as discussed above with respect to FIG. 18, the calibration target 2200 may include other indicia that facilitate aligning the reticule or portions thereof with the location of the x-ray spot.

Other patterns of materials may be used in a calibration target. Not all the pieces of the pattern need be made of distinct materials. Any pattern and combination of materials that produces different readings when an analyzer is aimed at different portions of the calibration target may be used.

Figure 20:
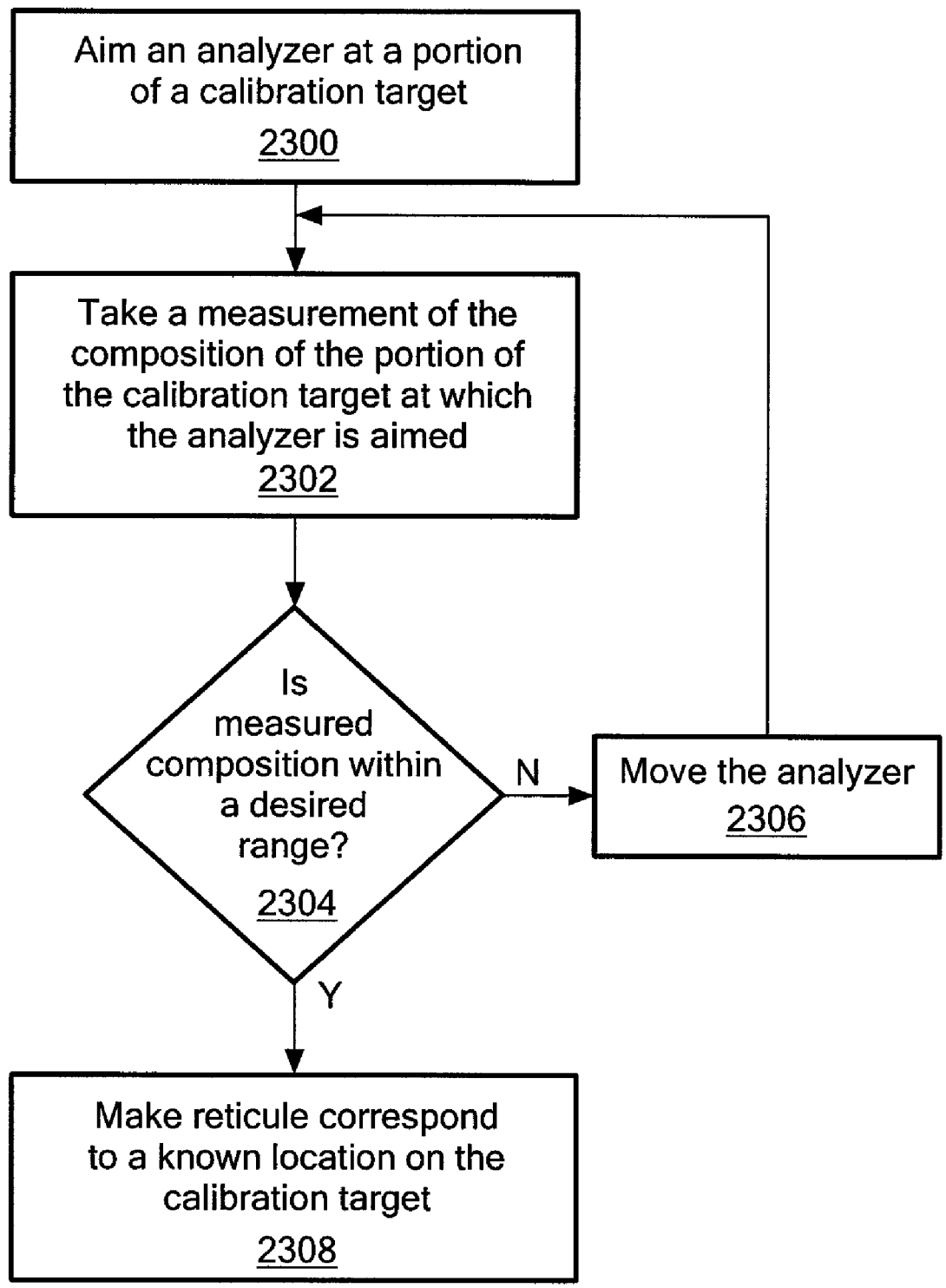
FIG. 20 contains a flowchart describing use of a calibration target to calibrate a reticule, according to one embodiment of the present invention.

The use of a calibration target to calibrate a reticule is described by a flowchart in FIG. 20. At 2300, an analyzer is aimed at a portion of a calibration target. At 2302, a measurement is taken of the composition of the portion of the calibration target, at which the analyzer is aimed. At 2304, if the measured composition is not within the desired range, control passes to 2306, where the analyzer is moved to another location on the calibration target, and then control returns to 2302. On the other hand, if the measured composition is within the desired range, control passes to 2308, where the reticule, or a portion thereof, is made to correspond to a known location on the calibration target, such as a plug or a point where vertexes of a plurality of pie-shaped pieces meet or overlap.

Figure 24:
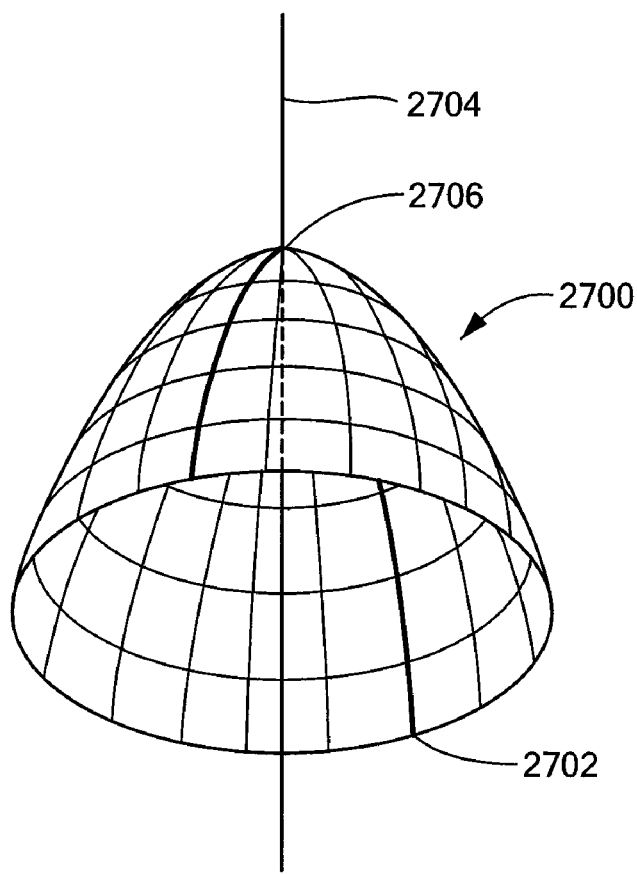
FIG. 24 is a schematic diagram of a model, according to which a reticule may be calibrated, according to one embodiment of the present invention.

Other methods for calibrating the location of a reticule involve modeling an expected x-ray fluorescence response function to a calibration target and aligning the reticule to measured readings, according to the model. One such embodiment uses a calibration target similar to the calibration target 2100 described above, with reference to FIG. 18. An expected x-ray fluorescence response function to the plug 2102 is shown graphically in FIG. 24. According to this model, the expected response function is a paraboloid 2700, i.e., a surface generated by rotating a parabola 2702 about its axis of symmetry 2704. The paraboloid 2700 is assumed to be aligned with the plug 2102, such that the axis 2704 is normal to the surface of the calibration target, and the axis 2704 passes through the center of the plug 2102. As described in more detail below: five readings are taken with the analyzer; an equation for the paraboloid 2700 is fitted to the five readings; the location of the apex 2706 of the paraboloid is determined from the equation; and the reticule is aligned with the apex of the paraboloid 2700.

The analyzer is aimed at the calibration target, such that the x-ray spot approximately corresponds with the location of the plug 2102. This may be accomplished by visually aligning the plug 2102 with an imaginary extension of the tube 308, as described above. The location on the image of the sample where the plug 2102 is visible is identified to the analyzer or external computer coupled to the analyzer's camera. In one embodiment, this is accomplished by causing a cross-hair cursor to correspond with the location of the plug 2102 in the image. For example, an operator may position the cursor in the image with a mouse or joystick. An x-ray fluorescence reading is taken at this location, which is referred to as the first location.

Figure 25:
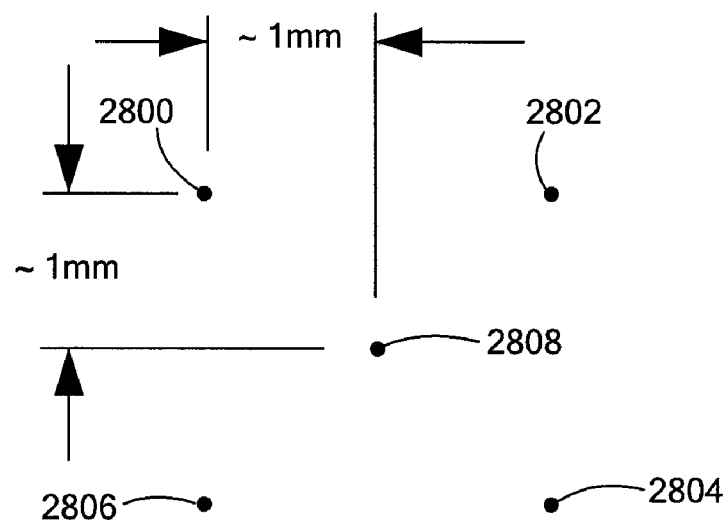
FIG. 25 is a schematic diagram of locations at which readings are taken to calibrate the reticule according to the model of FIG. 24.

The analyzer or external computer calculates at least four additional locations proximate the first location. In one embodiment, as shown schematically in FIG. 25, the four additional locations 2800, 2802, 2804 and 2806 are located at the corners of a square centered on the first location 2808. In one embodiment, for an approximately 3 mm x-ray spot on the sample, the four additional locations 2800-2806 are located at the corners of a 2 mm×2 mm square. Other regular or irregular shapes, and other sizes of shapes, may be used to select the additional locations.

The analyzer or external computer generates a reticule or other indicator on the screen at the location of one of the additional locations 2800-2806, and the operator repositions the analyzer so the plug 2102 is centered in the reticule. A second x-ray fluorescence reading is taken at this location. The process is repeated for each of the other additional locations 2800-2806, producing a total of five readings.

The surface of the paraboloid 2700 may be described by an equation:

$$z = A_0 + A_1 * \lfloor (x-X_0)^2 + (y-Y_0)^2 \rfloor$$

where x and y are coordinates of a point in an x-y plane and z is the height of the point over the x-y plane, i.e., the measured concentration of the material of the plug 2102. In this model, x and y are coordinates of the locations 2800-2808 in the plane of the locations. $X_0$ and $Y_0$ are coordinates of the apex 2706 of the paraboloid 2700, and $A_0$ and $A_1$ are constant coefficients, $A_0$ being the value of z at the apex 2706. The five readings are used to calculate the constant coefficients.

Once the coefficients are calculated, the coordinates of the apex 2706 are calculated, and the reticule is made to correspond to the location of the apex 2706.

Although a calibration method using a paraboloid is described, other methods may use two or more one-dimensional curves to model the response function. In one embodiment, two parabolas are used. In this embodiment, at least five sample points are taken to fit the curves.

The use of a calibration target and a model of a response function to calibrate a reticule is described by a flowchart in FIG. 26. At 2900, measurements are taken at a plurality of distinct locations on the calibration target. One of the measurements may be taken at a location that approximates a predetermined location, such as a plug, on the calibration target. The locations of the other measurements may be calculated based on the location of the predetermined location. At 2902, a curve representing an expected response function is fit to the measurements taken at 2900. The response function may be a three-dimensional function, such as a paraboloid, or two or more two-dimensional functions, such as parabolas. At 2904, the location of the reticule is made to correspond to a predetermined location on the curve, such as a peak in the curve.

A sheet of fluorescent material may be used to calibrate the size or shape of a reticule. In use, the front wall of the snout of an analyzer is pressed against the sheet of fluorescent material, and the analyzer is operated. The size and shape of the x-ray spot are made apparent by a spot of visible light given off by the fluorescent material where it is excited by the x-ray spot. The reticule may be made to correspond to the size and/or shape of the visible spot.

Other methods for calibrating the size or shape of the reticule include other devices for detecting x-rays, including active x-ray detectors, such as a silicon PIN diode, cadmium-telluride detector connected to an amplifier or proportional counter. The detector may be position sensitive in one or two dimensions.

Sample Image Annotated With Sample Analysis

An image of a sample produced by a camera within the snout of an analyzer may be automatically annotated with results of an analysis of the sample. As shown in FIG. 16, chemical constituents 1912 found in the sample under test may be displayed, such as in the upper-right corner of the touchscreen. Other information, such as the time and date 1914, on which the sample is analyzed, an automatically generated or user-entered sample number, the analyzer's serial number, model number and software revision level or warning messages generated by the analyzer (such as in connection with purging the instrument of ambient gas, as discussed below) may be included in the image. Furthermore, the user may enter text via the interface buttons 212 (FIG. 2) and/or a soft keyboard displayed on the touchscreen 210, and this text may also be used to annotate the image. In addition, non-textual information, such as a graph depicting a spectrum or chemical composition, may be included in the image. Pixels of the annotations may be opaque or translucent, and their colors may be dynamically chosen, as discussed above.

An analyzer may include a digital camera positioned to capture images of portions of a sample that are larger than the sample portion covered by the snout of the analyzer. The analyzer 200 of FIG. 2 has an optional external-view digital camera 216. A second external-view digital camera (not visible) may be included on the other side of the analyzer 200 to augment the view provided by the camera 216. Images provided by one or more such external-view cameras may be included with, associated with, or used instead of, images produced by a camera inside the snout of the analyzer 200.

Helium Purge

As noted, light elements (low Z elements) generally cannot be measured directly with portable XRF analyzers, because fluorescent x-rays with energies below about 2.5 KeV are attenuated in air. To overcome this problem, some prior-art portable XRF analyzers are fitted with gas connectors. Such an analyzer may be connected to a portable gas tank, such as a gas tank worn on the back of an operator of the analyzer. The tank contains helium, which is plumbed, via flexible tubing, to the analyzer. The analyzer uses the helium to purge air from a volume between the surface of the sample and the detector, such as a portion of the interior of the snout. Because helium is relatively transparent to fluorescent x-rays, such a "helium purge" system enables the analyzer to detect the light elements.

The tubing of such a "wearable" gas tank system can, however, pose a tripping danger to an operator. In addition, the tubing may become entangled with, or knock over, other equipment, as the operator moves about.

Figure 21:
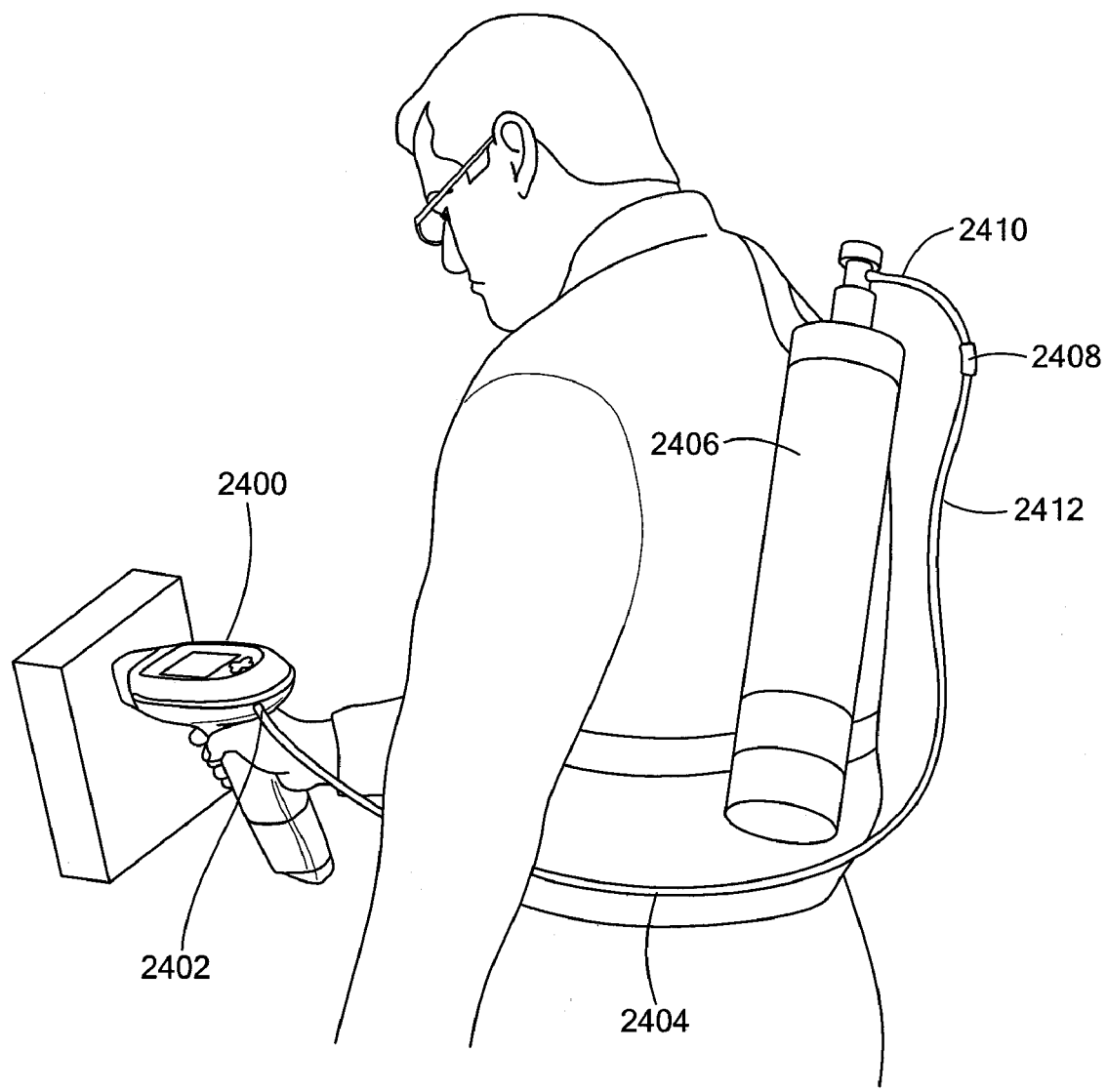
FIG. 21 is an illustration of a break-away coupling along a gas line to an XRF analyzer, according to one embodiment of the present invention.

Risks associated with long tubing may be minimized by including a break-away coupling along the gas line, between the tank and the analyzer. Such an arrangement is illustrated in FIG. 21. An analyzer 2400 includes a port 2402, to which a gas line, such as a flexible tube 2404, may be connected. The flexible tube 2404 is connected to a wearable gas tank 2406. The gas line includes a break-away coupling 2408. If more than a predetermined amount of tension is applied along the length of the flexible tube 2404, such as because the tube becomes caught on a fixed or heavy object, the break-away coupling 2408 separates into two sections. One section remains connected to the portion 2410 of the tube 2404 that is connected to the tank 2406. The other section 2412 remains connected to the portion 2412 of the tube 2404 that is connected to the analyzer 2400. Preferably, the section that remains connected to portion 2410 of the tube includes an automatic shut-off valve that is activated when the two portions 2410 and 2412 separate from each other.

Alternatively, the break-away coupling 2408 may be positioned elsewhere along the flexible tube 2404, such as proximate the analyzer 2400 or at the port on the analyzer. Optionally, more than one break-away coupling may be included along the length of the flexible tube 2304. In one embodiment, one break-away coupling is positioned proximate the tank, and another break-away coupling is positioned proximate the analyzer 2400.

Figure 22:
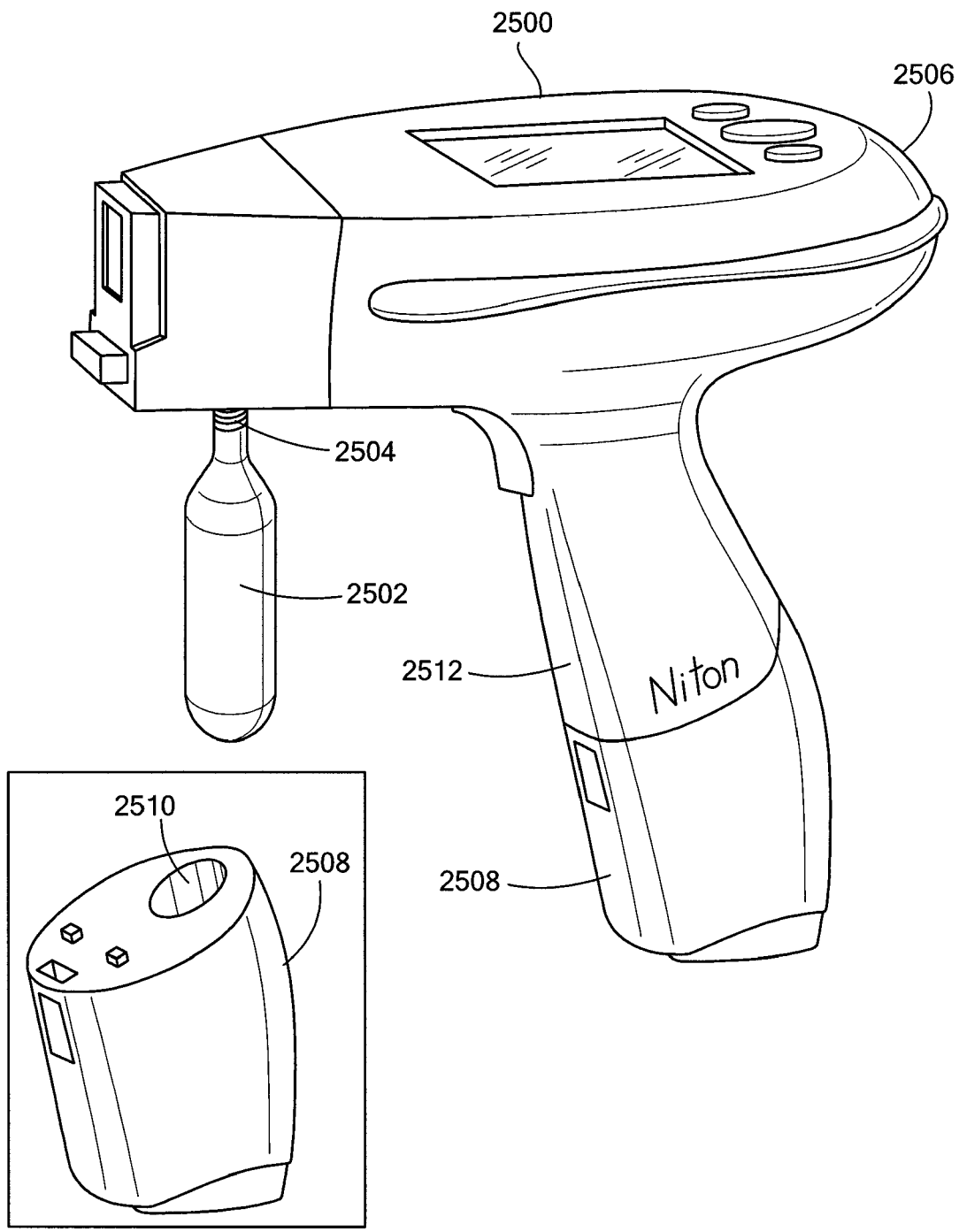
FIG. 22 is a perspective view of an analyzer to which a small gas tank is connected to provide a purge gas supply, according to one embodiment of the present invention.

Some users find wearable gas tanks to be awkward or uncomfortable. FIG. 22 illustrates an analyzer 2500 that includes a fitting (not visible), to which a small gas tank (also referred to as a gas "cartridge") 2502 may be connected to provide a gas supply, without the drawbacks of a wearable tank or a long flexible tube. The gas cartridge 2502 may be coupled to the analyzer 2500 by screwing a threaded portion 2504 on the neck of the cartridge into a corresponding female threaded portion of the coupling on the analyzer 2500. The coupling on the analyzer includes a sharp point or other suitable member to pierce a seal on the cartridge 2502, as the cartridge is threaded into the coupling, to allow gas to flow from the cartridge 2502 to the analyzer. The analyzer may include an appropriate shut-off valve, pressure regulator, flow-control valve, etc. as needed to control gas flow from the cartridge 2502. Such a gas cartridge 2502 may be easily replaced when the gas within the cartridge has been exhausted.

The coupling on the analyzer 2500 may be located elsewhere on the exterior or interior of the analyzer 2500. For example, the coupling may be located on the top of the snout or behind or below the back 2506 of the analyzer 2500. A portion of the housing of the analyzer (such as a hinged or removable door) may be opened to reveal a recess, into which the gas cartridge 2502 may be inserted, after which the door is closed.

The gas cartridge may be co-located with a rechargeable battery in a detachable portion 2508. In one such configuration (shown in the insert on FIG. 22), a bore 2510 receives a disposable or refillable gas cartridge. A suitable coupling in the bottom of the handle portion 2512 of the analyzer mates with the neck of the gas cartridge and pierces the seal when the detachable portion 2508 is attached to the handle portion 2512 of the analyzer 2500.

In another embodiment, instead of the bore 2510, a permanent, refillable gas cartridge (not shown) is located in the detachable portion 2508. In this case, the detachable portion 2508 includes a suitable neck or coupling to mate with a coupling in the bottom of the handle portion 2512. This gas cartridge may be refilled, such as when the detachable portion 2508 is detached from the rest of the analyzer 2500 to recharge the battery. A recharging station (not shown) may include a facility for recharging the battery and for refilling the gas cartridge. Such a recharging station may be coupled to a sufficiently large tank of gas to refill a plurality of gas cartridges in series or in parallel.

To minimize escape of the purge gas form the analyzer, the snout should include a relatively gas-tight chamber, into which the gas is introduced. Thus, a fluid communication path is established between the source of the gas (i.e., a wearable tank, a gas cartridge, a free-standing tank or any other suitable gas source, collectively hereinafter referred to as a tank) and the chamber. The chamber may include the collimated shutter 300 and other components described above.

Figure 23:
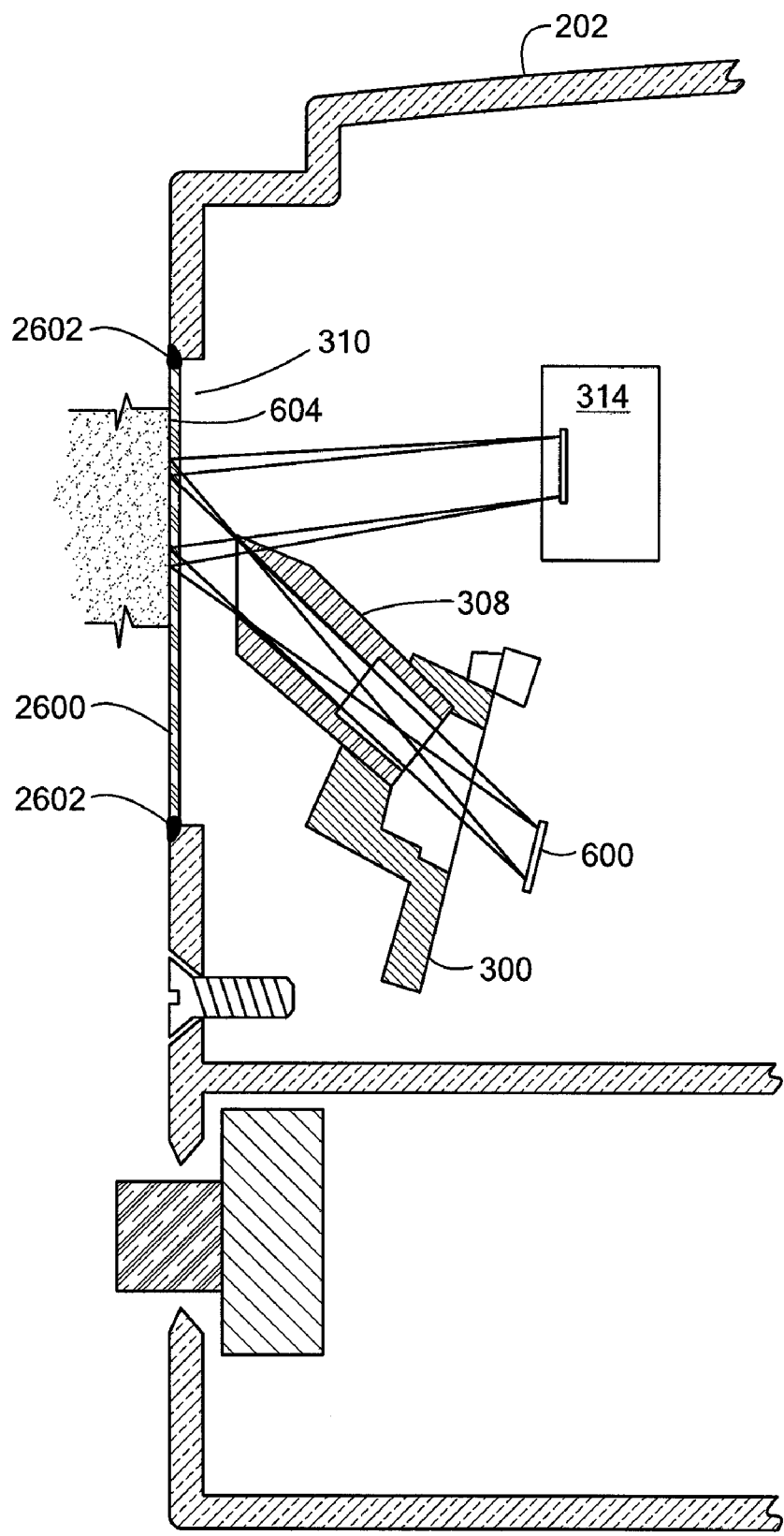
FIG. 23 is a cross-sectional view of a snout of the analyzer of FIG. 22, in which the window is fitted with a pane and a gas-tight gasket, according to one embodiment of the present invention.

As shown in FIG. 23, the window 310 may be fitted with a pane 2600, such as a sheet of polypropylene, fitted to the window opening with a gas-tight gasket 2602. The pane 2600 should be relatively transparent to the excitation beam and the fluorescent x-rays. The pane 2600 should exhibit a relatively high degree of resistance to embrittlement and degradation by the excitation energy beam and the fluorescent x-rays, as well as resisting thermal softening and deterioration from heat generated by exposure to these energy sources. A suitable material for the pane 2600 is available from Chemplex Industries, Inc., Palm City, Fla., under the tradename Prolene.

An analyzer may include an automatic mechanism for controlling the amount of purge gas that is admitted into the chamber, so that a minimum amount of gas is used, yet the interior of the chamber is sufficiently purged of ambient gas (air) to eliminate or adequately limit absorption of x-rays by the ambient gas. The analyzer may include a sensor for determining if an adequate (or inadequate) amount of purge gas is present in (or entering) the chamber or if an excessive (or a sufficiently small) amount of ambient gas is present in the chamber. This determination may be made directly (such as by testing the ambient or purge gas or by measuring the purge gas flow rate) or indirectly (such as by measuring a quantity that is correlated to the amount of ambient or purge gas). The analyzer may automatically control introduction of the purge gas, based on an output from the sensor. If insufficient purge gas or excessive ambient gas is detected in or entering the chamber, the analyzer may perform one or more actions. Among other actions, the analyzer may: refrain from storing results from an analysis, display a warning message along with results of the analysis or activate an audible alarm (such as a tone generator) or a visible alarm (such a light or an indicator on the touchscreen). An alarm may also be raised if an insufficient amount of gas can be provided by the tank, such as because the tank is empty.

In one embodiment, a flow rate regulator introduces the purge gas into the chamber at a predetermined constant volumetric rate, optionally automatically adjusted for changes in ambient atmospheric pressure. The rate may be selected to approximate or exceed a previously estimated, calculated or measured rate at which the purge gas escapes from the chamber. The flow rate may be restricted (such as to the predetermined amount) by a constriction in the fluid communication path and/or by a pressure regulator.

In another embodiment, the flow rate of the purge gas is automatically controlled in response to an output from a sensor. Thus, if excessive ambient gas is detected, or if insufficient purge gas is detected, the flow rate may be automatically increased. If a sufficiently small amount of ambient gas is detected, or if a sufficient amount of purge gas is detected, the flow rate may be automatically decreased, possibly to zero.

An electrically-actuated valve may be controlled by a processor or other control circuit in the analyzer to control the purge gas flow rate. The flow rate may be controlled by selectively opening and closing a binary valve (i.e., a valve that is either fully open or fully closed, with no intermediate settings) or by selectively operating a variable-opening valve. If a binary valve is used, particularly if such a valve is toggled rapidly, the fluid communication path may include an accumulator downstream from the valve to provide the purge gas at a more steady pressure.

The flow rate of the purge gas may be measured by a flow rate sensor in the fluid communication path. If the flow rate is measured to be less than a predetermined value, the flow rate may be automatically increased by adjusting or operating a valve.

The amount of purge gas in the chamber may be determined by measuring the pressure in the chamber. If the pressure is less than a predetermined valve, the purge gas flow rate may be automatically increased The amount of ambient gas in the chamber may be measured by measuring the amount of argon in the chamber using x-ray fluorescence, such as during a sample analysis, as described above. The amount of argon in the chamber is proportional to the amount of air in the chamber. Thus, argon may be used as a proxy for air in the chamber. In one embodiment, if the amount of argon detected in the chamber is greater than a predetermined value, automatically more purge gas may be introduced into the chamber or the flow rate may be increased.

The predetermined value may be a small value or zero, within the detection limits of the XRF analyzer. However, if silver is present in the path of the x-rays, the silver spectral lines (at 2.98 KeV and 3.15 KeV) may overlap with argon spectral lines (at 2.96 KeV and 3.19 KeV). Thus, as the argon is flushed from the chamber, the apparent height of the argon lines may be reduced, but not to zero. Thus, the predetermined value may be based on the expected heights of the silver lines after the argon has been purges from the chamber.

The helium concentration may be measured by making use of the high thermal conductivity of helium, compared to air. In one embodiment, the amount of electrical current needed to maintain a constant temperature of a thermistor that is mounted in the chamber is monitored. If the amount of current varies, the concentration of helium may be assumed to have varied, and more or less helium may be introduced to compensate.

Aspects of the analyzers described above may be used in conjunction with other types of analyzers, such as analyzers that employ arc/spark optical emission spectroscopy (OES), laser-induced breakdown spectroscopy (LIBS) or a combination thereof. These aspects include, but are not limited to: the detector collimator, digital camera, image correction, image annotation, co-archiving of sample image and analysis data, reticule, reticule calibration, gas purge (possibly using argon or another gas), break-away coupling, gas cartridge and purge gas flow control.

A chemical composition analyzer has been described as including a processor controlled by instructions stored in a memory. The memory may be random access memory (RAM), read-only memory (ROM), flash memory or any other memory, or combination thereof, suitable for storing control software or other instructions and data. Some of the functions performed by the analyzer have been described with reference to flowcharts. Those skilled in the art should readily appreciate that functions, operations, decisions, etc. of all or a portion of each block, or a combination of blocks, of the flowcharts may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various illustrative data structures, one skilled in the art will recognize that the system may be embodied using a variety of data structures. Furthermore, disclosed aspects, or portions of these aspects, may be combined in ways not listed above. Accordingly, the invention should not be viewed as limited, except by the scope and spirit of the appended claims.

What is claimed is:

1. An analyzer for analyzing composition of a sample, comprising:
 a hand-held, self-contained, test instrument that includes:
  a source for producing a beam of penetrating radiation for illuminating a spot on at least a portion of the sample, thereby causing the sample to emit fluoresced radiation characteristic of elements in the sample;
  a collimator for the beam having a distal exit aperture characterized by a transverse dimension, the distal exit disposed at a distance from the sample no greater than about twice the transverse dimension;
  a detector positioned to receive the fluoresced radiation for producing an output signal representative of spectral data;
  a processor coupled to the detector and programmed to process the output signal from the detector;
  a battery powering the source and the processor; and
  a second collimator for the beam having a second distal exit aperture characterized by a second transverse dimension, the second distal exit being disposed, when the beam passes through the second collimator to illuminate the spot, at a distance from the sample no greater than about twice the second transverse dimension.

2. An analyzer, as defined in claim 1, wherein the distal exit aperture is substantially parallel to a surface of the sample to be analyzed and the second distal exit aperture is substantially parallel to the surface of the sample.

3. An analyzer, as defined in claim 1, wherein the transverse dimension is less than about 8 mm and the second transverse dimension is less than about 3 mm.

4. An analyzer, as defined in claim 1, wherein the transverse dimension is less than about 3 mm and the second transverse dimension is less than about 1 mm.

5. An analyzer, as defined in claim 1, wherein the collimator and the second collimator move together between at least two positions such that, in a first position of the at least two positions, the beam passes through the collimator to illuminate the spot and, in a second position of the at least two positions, the beam passes through the second collimator to illuminate the spot.

6. An analyzer, as defined in claim 5, further comprising a shutter disposed between the source and the sample and operative to selectively allow or prevent the beam to illuminate the spot.

7. An analyzer, as defined in claim 6, wherein the collimator, the second collimator and the shutter move together among at least three positions such that, in at least one of the positions, the shutter prevents the beam from illuminating the spot.

8. The analyzer of claim 1, further comprising a camera configured to acquire an image of at least a portion of the sample.

9. The analyzer of claim 8, further comprising a display screen on which the image is displayed.

10. The analyzer of claim 8, wherein the processor is programmed to insert into the image a visual indication of the illuminated spot on the sample.

11. The analyzer of claim 8, further comprising a laser oriented to project a visible spot on the sample in a location that corresponds to the spot of penetrating radiation.

* * * * *